United States Patent
Marubashi

(10) Patent No.: US 11,963,555 B2
(45) Date of Patent: Apr. 23, 2024

(54) CONTROLLER FOR INHALATION DEVICE

(71) Applicant: Japan Tobacco Inc., Tokyo (JP)

(72) Inventor: Keiji Marubashi, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 481 days.

(21) Appl. No.: 17/189,285

(22) Filed: Mar. 2, 2021

(65) Prior Publication Data
US 2021/0274850 A1  Sep. 9, 2021

(30) Foreign Application Priority Data

Mar. 5, 2020 (JP) .................. 2020-038095

(51) Int. Cl.
*A24F 40/57* (2020.01)
*A24F 40/53* (2020.01)

(52) U.S. Cl.
CPC .............. *A24F 40/57* (2020.01); *A24F 40/53* (2020.01)

(58) Field of Classification Search
None
See application file for complete search history.

(56) References Cited

U.S. PATENT DOCUMENTS

| | | | |
|---|---|---|---|
| 10,299,514 B2 | 5/2019 | Bilat et al. | |
| 10,477,893 B2 | 11/2019 | Lord | |
| 10,925,315 B2 | 2/2021 | Bilat | |
| 2015/0237917 A1 | 8/2015 | Lord | |
| 2018/0020735 A1* | 1/2018 | Bilat | H05B 1/0277 |
| | | | 131/328 |
| 2018/0303161 A1* | 10/2018 | Bilat | H05B 1/0297 |
| 2020/0352247 A1 | 11/2020 | Yamada et al. | |

FOREIGN PATENT DOCUMENTS

| | | |
|---|---|---|
| CN | 109043675 A | 12/2018 |
| CN | 110179160 A | 8/2019 |
| JP | 2015-517312 A | 6/2015 |
| JP | 2015-536648 A | 12/2015 |
| JP | 2018-514191 A | 6/2018 |
| JP | 6651667 B1 | 2/2020 |
| WO | 2019/146063 A1 | 8/2019 |

OTHER PUBLICATIONS

Office Action dated Jun. 15, 2020, received for JP Application 2020-038095, 10 pages including English Translation.
Extended European Search Report dated Aug. 2, 2021 in European Patent Application No. 21158645.8, 8 pages.

* cited by examiner

*Primary Examiner* — Cynthia Szewczyk
(74) *Attorney, Agent, or Firm* — XSENSUS LLP

(57) ABSTRACT

The present invention provides a controller for an inhalation device, comprising: a power supplier configured to supply power to a heater used to heat and atomize an aerosol source; a detection circuit configured to detect a resistance value of the heater; and a processor configured to execute heating processing of heating the aerosol source by controlling the power supplier in accordance with reception of an atomization request of the aerosol source, wherein the processor controls the heating processing based on the resistance value of the heater detected using the detection circuit, a reference temperature of the heater, and a reference resistance value of the heater, and updates the reference resistance value by the resistance value of the heater detected using the detection circuit after an end of the heating processing and before the reception of the next atomization request.

12 Claims, 16 Drawing Sheets

CONTROLLER FOR INHALATION DEVICE

CROSS REFERENCES TO RELATED APPLICATION

The present invention contains subject matter related to Japanese Patent Application No. 2020-038095 filed in the Japan Patent Office on Mar. 5, 2020, the entire contents of which are incorporated herein by reference.

BACKGROUND OF THE INVENTION

Field of the Invention

The present invention relates to a controller for an inhalation device.

Description of the Related Art

Japanese Patent Laid-Open No. 2018-514191 describes an aerosol generation system including an electric heater configured to heat an aerosol forming base. The system detects, based on a change in the resistance of the heater, an increase of the speed of the temperature change of the heater which occurs when the aerosol forming base in a cartridge is nearly used up. More specifically, a resistance R1 formed by a parasitic resistance RP of an electrical contact of the heater and a resistance R0 of a heater filament is measured as an initial resistance value before any heating is performed (before the heater is activated for the first time), and a change ΔR (=R2−R1) of the resistance of the heater at time t1 from supply of power to the heater is calculated using the initial resistance value R1 as a reference. R2 is the resistance of the heater at time t1. Using the calculated change ΔR of the resistance of the heater, an abrupt increase in the temperature of the heater, which indicates a dry state of the heater filament, is detected.

In Japanese Patent Laid-Open No. 2018-514191, the resistance value R1 serving as the reference of heater temperature detection is measured before any heating is performed (before the heater is activated for the first time) and used in all subsequent heater temperature detection processes. However, the present inventor found that the reference resistance value of the heater corresponding to a predetermined temperature (reference temperature) of the heater varies in, for example, each puff operation of a user because of the parasitic resistance (contact resistance) of the electrical contact of the heater, and the like. If the reference resistance value corresponding to the reference temperature of the heater changes, it may be difficult to accurately detect the temperature of the heater.

SUMMARY OF THE INVENTION

The present invention provides a technique advantageous in, for example, accurately detecting the temperature of a heater that heats an aerosol source.

According to one aspect of the present invention, there is provided a controller for an inhalation device, comprising: a power supplier configured to supply power to a heater used to heat and atomize an aerosol source; a detection circuit configured to detect a resistance value of the heater; and a processor configured to execute heating processing of heating the aerosol source by controlling the power supplier to supply the power to the heater in accordance with reception of an atomization request of the aerosol source, wherein the processor controls the heating processing based on the resistance value of the heater detected using the detection circuit during the heating processing, a reference temperature of the heater, and a reference resistance value of the heater at the reference temperature, and updates the reference resistance value by the resistance value of the heater detected using the detection circuit after an end of the heating processing and before the reception of the next atomization request.

Further features of the present invention will become apparent from the following description of exemplary embodiments with reference to the attached drawings.

DESCRIPTION OF THE EMBODIMENTS

Figure 1:
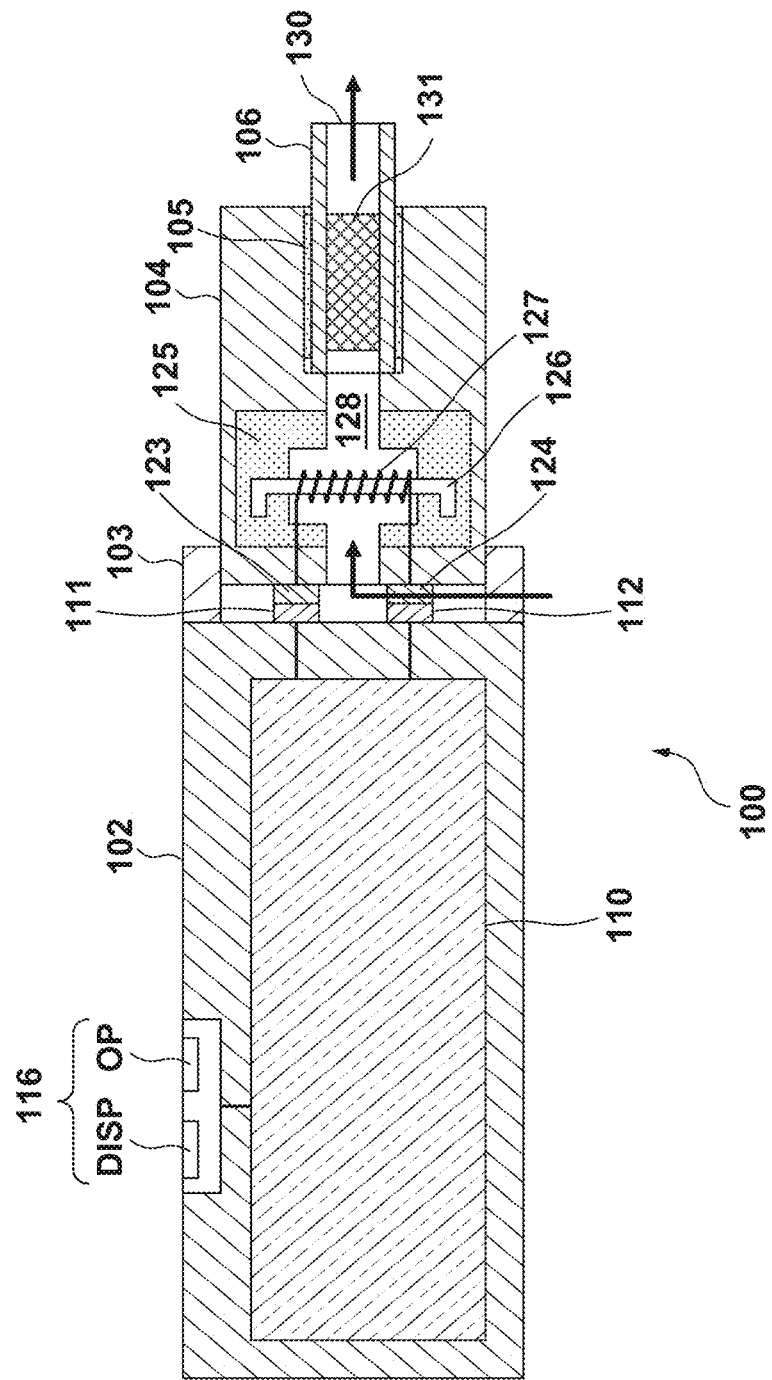
FIG. 1 is a view schematically showing the arrangement of an inhalation device according to an embodiment.

Hereinafter, embodiments will be described in detail with reference to the attached drawings. Note that the following embodiments are not intended to limit the scope of the claimed invention, and limitation is not made an invention that requires all combinations of features described in the embodiments. Two or more of the multiple features described in the embodiments may be combined as appropriate. Furthermore, the same reference numerals are given to the same or similar configurations, and redundant description thereof is omitted.

FIG. 1 schematically shows the arrangement of an inhalation device (inhalator) 100 according to an embodiment. The inhalation device can be configured to provide a gas containing an aerosol or a gas containing an aerosol and a flavor substance to a user via a mouthpiece portion 130 in accordance with an inhalation operation of the user. The inhalation device 100 can include a controller 102 and an atomizer 104. The inhalation device 100 can include a holding portion 103 that holds the atomizer 104 in a detachable state. The controller 102 can be understood as an inhalation device controller. The atomizer 104 can be configured to atomize an aerosol source. The aerosol source can be, for example, a liquid such as a polyhydric alcohol such as glycerin or propylene glycol. Alternatively, the aerosol source may contain a drug. The aerosol source may be a liquid, a solid, or a mixture of a liquid and a solid. A vapor source such as water may be used in place of the aerosol source.

The inhalation device 100 may further include a capsule 106 including a flavor source 131, and the atomizer 104 can include a capsule holder 105 that holds the capsule 106 in a detachable state. The capsule holder 105 may be included not in the atomizer 104 but in the controller 102. The flavor source 131 can be, for example, a molded body formed by molding a tobacco material. Alternatively, the flavor source 131 may be formed by a plant (for example, mint, herb, Chinese herb, coffee bean, and the like) other than tobacco. A flavor such as menthol may be added to the flavor source. The flavor source 131 may be added to the aerosol source.

The controller 102 can include an electric component 110. The electric component 110 can include a user interface 116. Alternatively, it may be understood that the controller 102 includes the electric component 110 and the user interface 116. The user interface 116 can include, for example, a display unit DISP (for example, a light emitting element such as an LED and/or an image display device such as an LCD) and/or an operation unit OP (for example, a switch such as a button switch and/or a touch display).

The holding portion 103 of the controller 102 can include a first electrical contact 111 and a second electrical contact 112. In a state in which the atomizer 104 is held by the holding portion 103, the first electrical contact 111 of the holding portion 103 can contact a third electrical contact 123 of the atomizer 104, and the second electrical contact 112 of the holding portion 103 can contact a fourth electrical contact 124 of the atomizer 104. The controller 102 can supply power to the atomizer 104 via the first electrical contact 111 and the second electrical contact 112.

The atomizer 104 can include the third electrical contact 123 and the fourth electrical contact 124 described above. In addition, the atomizer 104 can include a heater 127 that heats the aerosol source, a container 125 that holds the aerosol source, and a transport portion (wick) 126 that transports the aerosol source held by the container 125 to a heating area by the heater 127. At least a part of the heating area can be arranged in a channel 128 provided in the atomizer 104. The first electrical contact 111, the third electrical contact 123, the heater 127, the fourth electrical contact 124, and the second electrical contact 112 form a current path configured to flow a current to the heater 127. The transport portion 126 can be made of, for example, a fiber material or a porous material.

As described above, the atomizer 104 can include the capsule holder 105 that detachably holds the capsule 106. In an example, the capsule holder 105 can hold the capsule 106 such that a part of the capsule 106 is stored in the capsule holder 105 or the atomizer 104, and the other part is exposed. The user can inhale a gas containing an aerosol by holding the mouthpiece portion 130 in the mouth. When the mouthpiece portion 130 is provided in the detachable capsule 106, the inhalation device 100 can be kept clean.

When the user holds the mouthpiece portion 130 in the mouth and performs an inhalation operation, air flows into the channel 128 of the atomizer 104 via an opening (not shown), and an aerosol generated by heating the aerosol source by the heater 127 is transported to the mouthpiece portion 130, as indicated by arrows. In the arrangement in which the flavor source 131 is arranged, a flavor substance generated from the flavor source 131 is added to the aerosol, transported to the mouthpiece portion 130, and inhaled into the mouth of the user.

Figure 2:
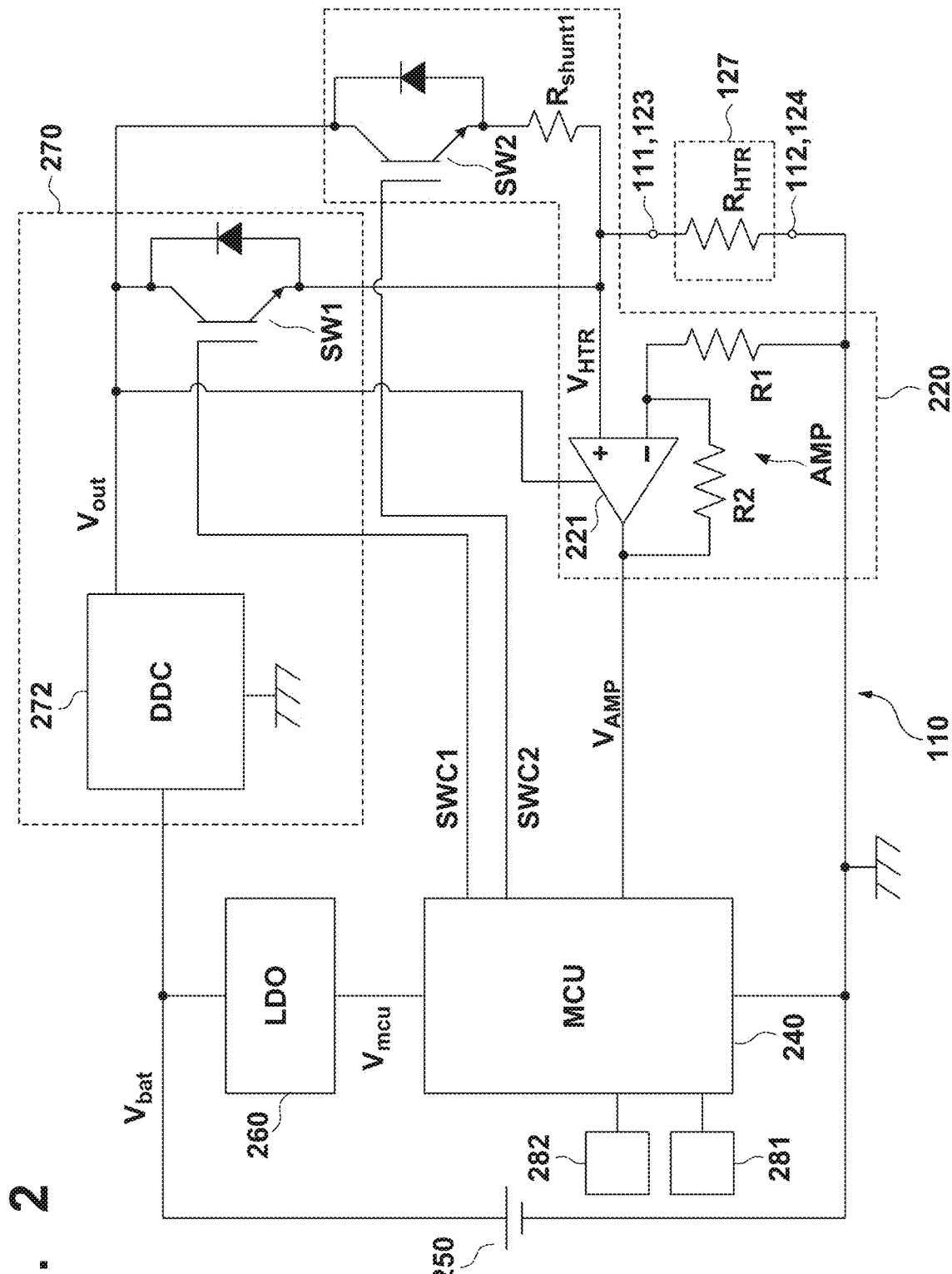
FIG. 2 is a view showing the first arrangement example of an electric component.

FIG. 2 shows the first arrangement example of the electric component 110. The electric component 110 can include a power supply (battery) 250, a power supply unit (power supplier) 270 that supplies power to (the heater 127 of) the atomizer 104, a detection circuit 220 configured to detect the resistance value of the heater 127, and a processor 240 that generates a control signal in accordance with information obtained using the detection circuit 220. The heater 127 has a resistance value $R_{HTR}$ that changes depending on the temperature of the heater 127.

The power supply unit 270 can include a switch SW1 arranged in a current path configured to supply a current to the heater 127. Opening/closing (off/on) of the switch SW1 can be controlled by a control signal SWC1 generated by the processor 240. The power supply unit 270 can include, for example, a voltage converter 272 that converts a power supply voltage $V_{bat}$ supplied from the power supply 250 into a heater driving voltage $V_{out}$. The switch SW1 can be arranged to form a current path configured to supply a current to the heater 127 between the ground line and the supply line of the heater driving voltage $V_{out}$. The switch SW1 can be arranged, for example, between the heater 127 and the supply line of the heater driving voltage $V_{out}$.

The detection circuit 220 can include a shunt resistor $R_{shunt1}$ and a switch SW2, which are arranged, in series with the heater 127, between the ground line and the supply line of the heater driving voltage $V_{out}$. Also, the detection circuit 220 can include an amplifier AMP that detects a voltage $V_{HTR}$ applied to the heater 127. Here, the resistance value of the shunt resistor $R_{shunt1}$ will be expressed as $R_{shunt1}$, like the reference symbol. The amplifier AMP includes, for example, a differential amplifier 221 including a noninverting input terminal, an inverting input terminal, and an output terminal, a resistive element R1 that connects the inverting input terminal and the ground line, and a resistive element R2 that connects the inverting input terminal and the output terminal, and the voltage $V_{HTR}$ can be input to the noninverting input terminal. In this arrangement example, if the resistance value of the resistive element R1 is expressed as R1, and the resistance value of the resistive element R2 is expressed as R2, an amplification factor A of the amplifier AMP is (1+R2/R1). The switch SW2 can be controlled by a control signal SWC2 generated by the processor 240.

To detect the resistance value $R_{HTR}$ of the heater 127, the switch SW1 is turned off, and the switch SW2 is turned on. At this time, letting $I_{HTR}$ be a current flowing to $R_{HTR}$, equation (1) is obtained.

$$R_{HTR}=V_{HTR}/I_{HTR}=V_{HTR}\cdot(R_{HTR}+R_{shunt1})/V_{out} \quad (1)$$

When equation (1) is deformed, equation (2) for gibing $R_{HTR}$ is obtained.

$$R_{HTR}=R_{shunt1}\cdot V_{HTR}/(V_{out}-V_{HTR}) \quad (2)$$

An output voltage $V_{AMP}$ of the amplifier AMP of the detection circuit 220 is given by $$V_{AMP}=A\cdot V_{HTR} \quad (3)$$

When equation (3) is deformed, equation (4) for giving $V_{HTR}$ is obtained.

$$V_{HTR}=V_{AMP}/A \quad (4)$$

Hence, the resistance value $R_{HTR}$ of the heater 127 can be obtained in accordance with equations (2) and (4).

The processor 240 can include an input terminal to which the output voltage $V_{AMP}$ of the amplifier AMP of the detection circuit 220 is input, and an A/D converter that converts an analog signal that is a voltage input to the input terminal into a digital signal. The processor 240 can generate a control signal in accordance with information (here, $V_{AMP}$) obtained using the detection circuit 220. The control signal can be, for example, the control signal SWC1 but can include another control signal (for example, a control signal that controls the display unit DISP).

The processor 240 can be formed by, for example, an MCU (Micro Controller Unit). However, the processor 240 may be formed by an MCU and an analog circuit. To the processor 240, a voltage $V_{mcu}$ can be supplied from a voltage conversion circuit 260 such as an LDO (Low DropOut) that converts the power supply voltage $V_{bat}$ into the voltage $V_{mcu}$ for the processor 240. The processor 240 can calculate the resistance value $R_{HTR}$ of the heater 127 in accordance with equations (2) and (4) based on $R_{shunt1}$ that is a known value, $V_{out}$, and $V_{AMP}$ that is supplied from the amplifier AMP.

The processor 240 can calculate the temperature of the heater 127 in accordance with equation (5) based on the resistance value $R_{HTR}$ of the heater 127.

$$T=T_{ref}+(1/\alpha)\cdot(R_{HTR}-R_{ref})\cdot(1/R_{ref})\cdot 10^6 \quad (5)$$

In equation (5), $T_{ref}$ is the reference temperature of the heater 127. $R_{ref}$ is the reference resistance value of the heater 127, and this is the resistance value $R_{HTR}$ of the heater 127 at the reference temperature. $\alpha$ is the temperature coefficient [ppm/° C.] of the heater 127. Here, the reference temperature can be an arbitrary temperature, and can be stored in the memory of the processor 240 in association with (in linkage with) the reference resistance value. As the reference temperature, for example, a temperature set in advance may be used, as will be described later, or the temperature of the heater 127 obtained when acquiring the reference resistance value may be used. The temperature of the heater 127 obtained when acquiring the reference resistance value can be converted from the temperature of an arbitrary portion in the inhalation device 100 (for example, a temperature detected by a temperature sensor 282 to be described later).

Based on the temperature of the heater 127, the processor 240 can generate the control signal SWC1 used to control the switch SW1 such that the temperature of the heater 127 matches a target temperature. The processor 240 receives a signal from the operation unit OP of the user interface 116, and provides a signal for display control to the display unit DISP of the user interface 116. The electric component 110 can include a puff sensor (for example, a pressure sensor) 281 that detects the puff operation of the user, and the temperature sensor 282 that detects the temperature of a predetermined portion of the electric component 110. The temperature sensor 282 may be incorporated in the puff sensor 281, the power supply 250, or the processor 240.

Figure 3:
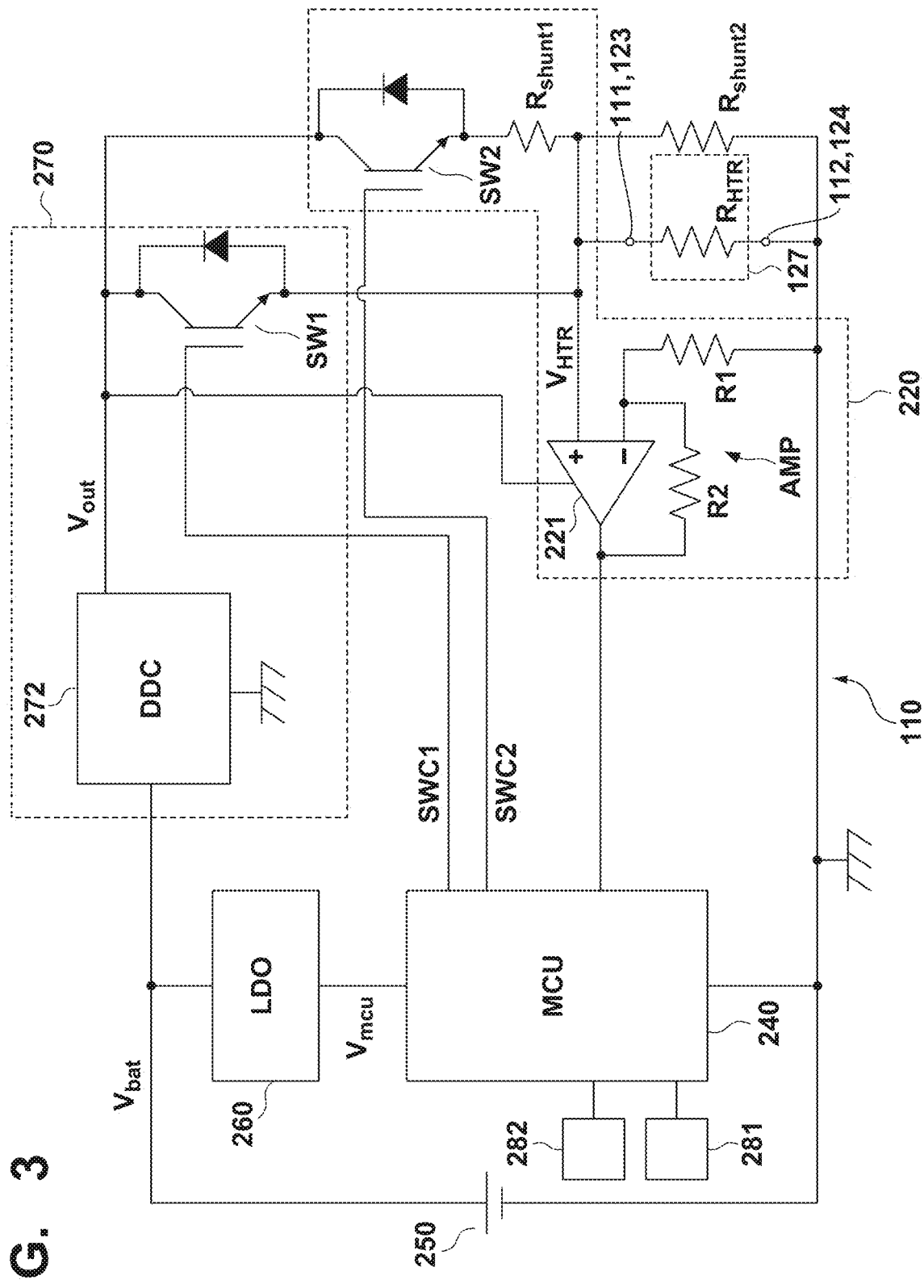
FIG. 3 is a view showing the second arrangement example of the electric component.

FIG. 3 is a view showing the second arrangement example of the electric component 110. The second arrangement example is different from the first arrangement example in that a shunt resistor $R_{shunt2}$ is provided, in series with the shunt resistor $R_{shunt1}$, between a shunt resistor $R_{shunt1}$ and the ground line, and the rest is the same as in the first arrangement example. Here, the resistance value of the shunt resistor $R_{shunt2}$ will be expressed as $R_{shunt2}$, like the reference symbol. The resistance value $R_{shunt2}$ is sufficiently larger than the resistance value $R_{HTR}$. Hence, equation (2) can be used in the calculation of the resistance value $R_{HTR}$.

Figure 4:
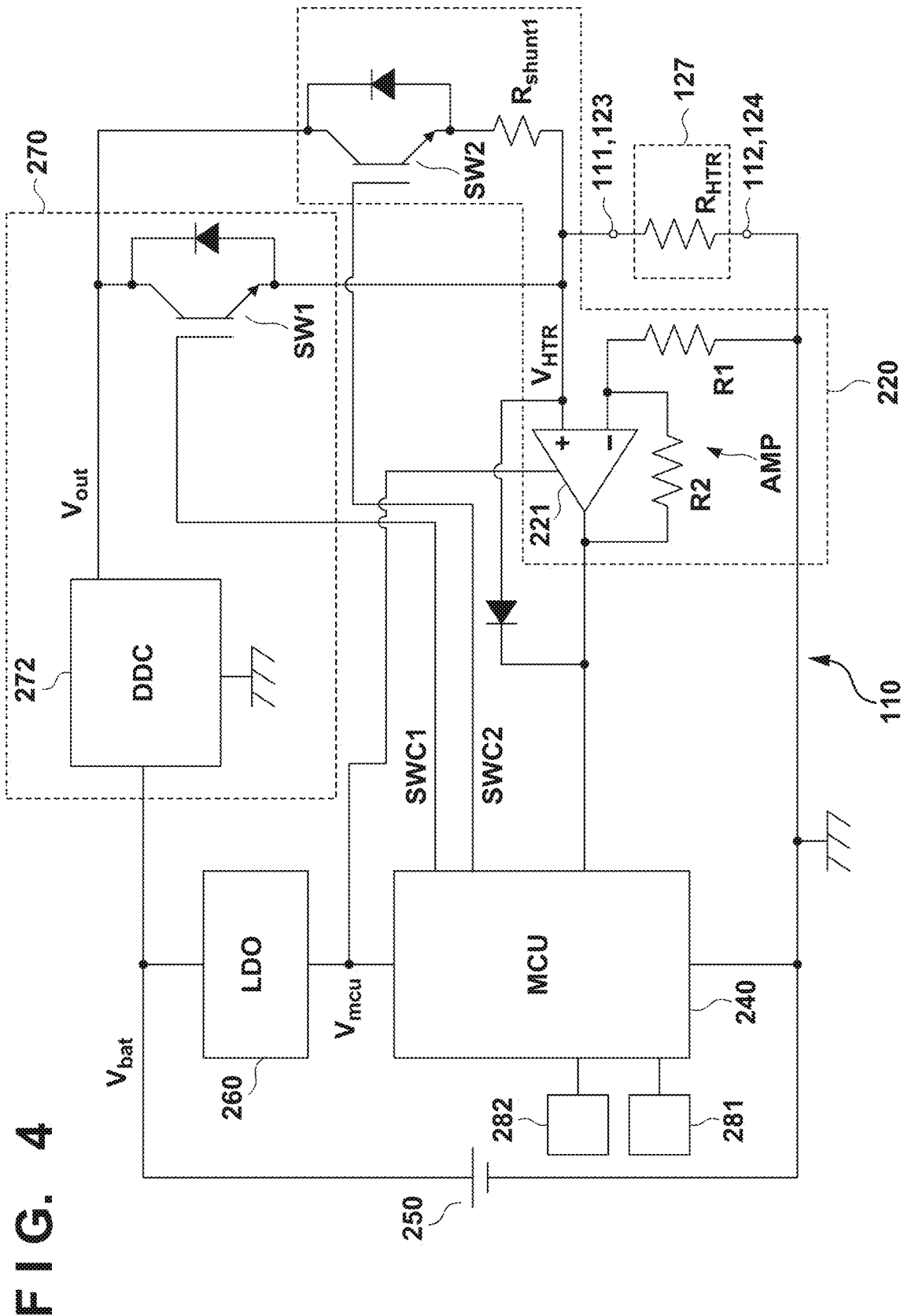
FIG. 4 is a view showing the third arrangement example of the electric component.

FIG. 4 is a view showing the third arrangement example of the electric component 110. The third arrangement example is different from the first arrangement example in that the voltage $V_{mcu}$ is supplied to the power supply terminal of the differential amplifier 221. The shunt resistor $R_{shunt2}$ as in the second arrangement example may be added to the third arrangement example. Between the noninverting input terminal and the output terminal of the differential amplifier 221, a diode can be arranged in the forward direction from the noninverting input terminal to the output terminal.

Figure 5A:
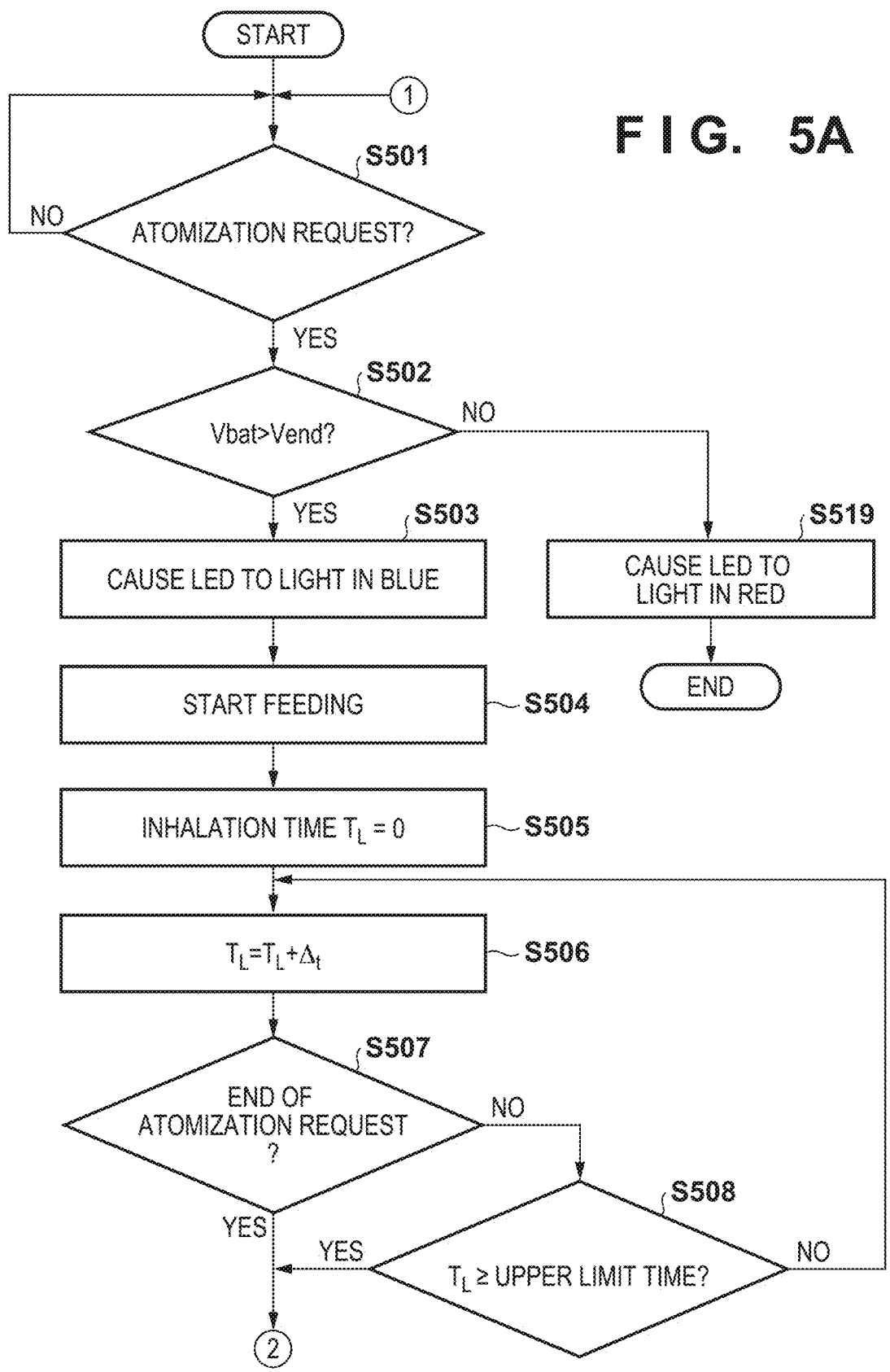
FIGS. 5A-5B are flowcharts showing the operation of the inhalation device according to an embodiment.
Figure 5B:
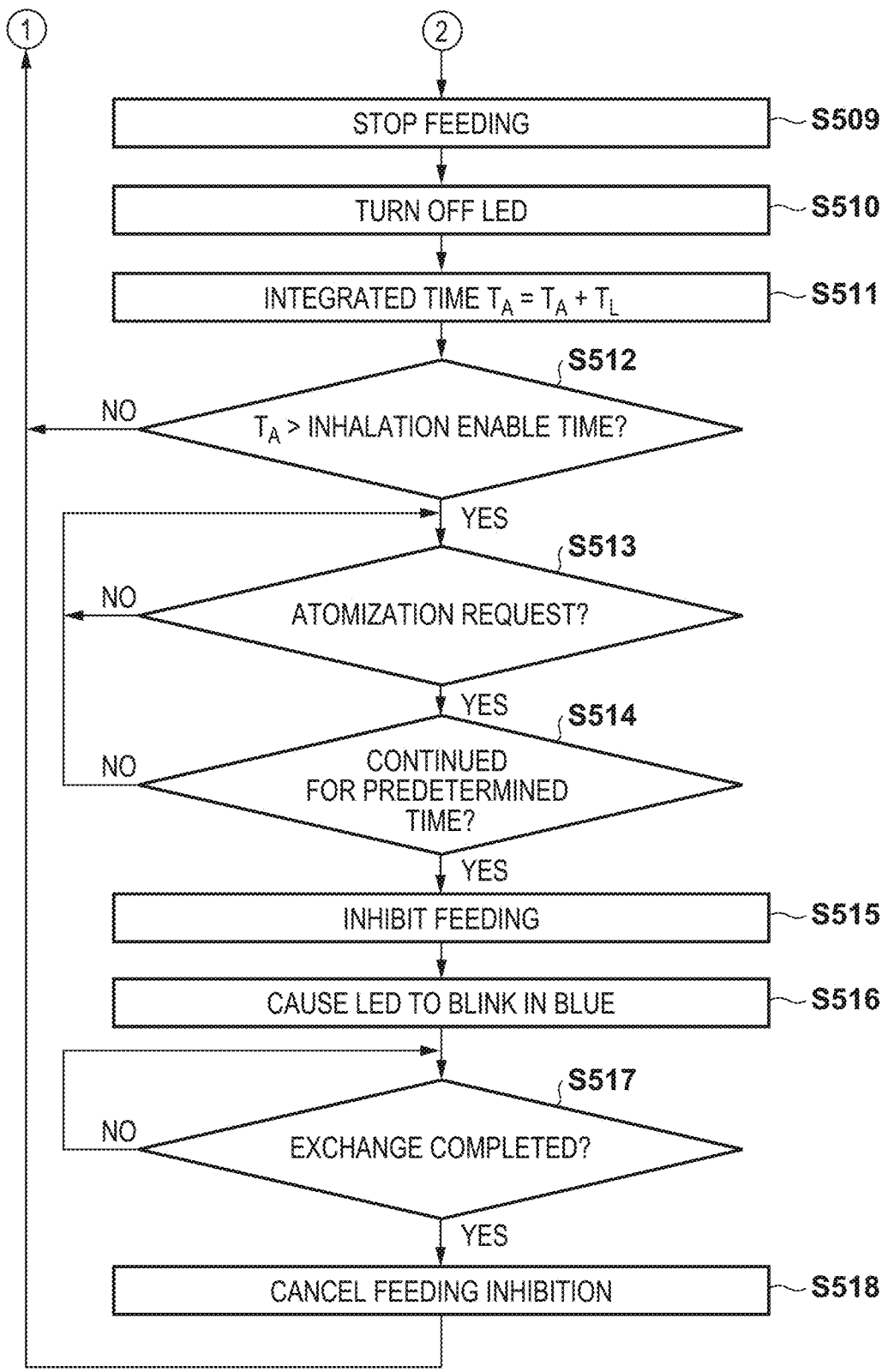

FIGS. 5A-5B show the operation of the inhalation device 100. This operation is controlled by the processor 240. The processor 240 includes a memory that stores a program, and a CPU that operates in accordance with the program. In step S501, the processor 240 waits for reception of an atomization request, and upon receiving an atomization request, executes step S502. The atomization request is a request for operating the atomizer 104, more specifically, controlling the heater 127 within a target temperature range to generate an aerosol from the aerosol source. The atomization request can be an operation of detecting, by the puff sensor 281, that the user has performed the inhalation operation (puff operation) via the mouthpiece portion 130, and notifying, by the puff sensor 281, the processor 240 of the detection (for example, transmission of a detection signal). Alternatively, the atomization request can be an operation of notifying, by the operation unit OP, the processor 240 that the user has operated the operation unit OP (for example, transmission of an operation signal). In the following description, during the inhalation operation of the user or during the operation of the operation unit OP by the user, the atomization request is continuously transmitted from the puff sensor 281 or the operation unit OP, and when the user ends the inhalation operation or the operation of the operation unit OP, (transmission of) the atomization request is ended.

In step S502, the processor 240 acquires the power supply voltage $V_{bat}$ from a power supply management circuit (not shown), and determines whether the power supply voltage $V_{bat}$ is higher than a discharge end voltage $V_{end}$ (for example, 3.2 V). That the power supply voltage $V_{bat}$ is equal to or lower than the discharge end voltage $V_{end}$ means that the remaining dischargeable amount of the power supply 250 is not sufficient. Hence, if the power supply voltage $V_{bat}$ is equal to or lower than the discharge end voltage $V_{end}$, in step S519, the processor 240 makes a notification to promote charge of the power supply 250 using the display unit DISP of the user interface 116. If the display unit DISP includes an LED, this notification can be causing the LED to light in red. On the other hand, if the power supply voltage $V_{bat}$ is higher than the discharge end voltage $V_{end}$, the processor 240 executes heating processing. Heating processing is processing of controlling the power supply unit 270 to supply power to the heater 127 and heating the aerosol source in accordance with reception of the aerosol source atomization request, and can include steps S503 to S507.

In step S503, using the display unit DISP of the user interface 116, the processor 240 can make a notification representing that a normal operation is possible. If the display unit DISP includes an LED, this notification can be causing the LED to light in blue. Next, in step S504, the processor 240 starts power feeding control (power supplying control) for the heater 127. The power feeding control for the heater 127 includes temperature control of controlling the heater 127 within a target temperature range. The temperature control can include feedback control of detecting the temperature of the heater 127 by detecting the resistance value $R_{HTR}$ of the heater 127, and controlling opening/closing of the switch SW1 by the control signal SWC1 based on the detection result.

Next, in step S505, the processor 240 resets an inhalation time $T_L$ to 0. After that, in step S506, the processor 240 adds Δt to the inhalation time $T_L$. Δt corresponds to the time interval between execution of step S506 and the next execution of step S506.

Next, in step S507, the processor 240 determines whether the atomization request has ended. If the atomization request has ended, in step S509, the processor 240 stops the power feeding control for the heater 127. On the other hand, if the atomization request has not ended, in step S508, the processor 240 determines whether the inhalation time $T_L$ has reached an upper limit time. If the inhalation time $T_L$ has not reached the upper limit time, the process returns to step S506. As an example, the upper limit time may be 2.0 to 2.5 sec.

Next to step S509, in step S510, the processor 240 turns off the LED that is lighting in blue. Next, in step S511, the processor 240 updates an integrated time $T_A$. More specifically, in step S511, the inhalation time $T_L$ is added to the integrated time $T_A$ at the current point of time. The integrated time $T_A$ can be an integrated time when the capsule 106 was used for inhalation, in other words, an integrated time when the aerosol was inhaled via the flavor source 131 of the capsule 106.

In step S512, the processor 240 determines whether the integrated time $T_A$ is not more than an inhalation enable time (for example, 120 sec). If the integrated time $T_A$ is not more than the inhalation enable time, this means that the capsule 106 can still provide the flavor substance. In this case, the process returns to step S501. If the integrated time $T_A$ is more than the inhalation enable time, in step S513, the processor 240 waits for generation of the atomization request. If the atomization request is generated, in step S514, the processor 240 waits for continuation of the atomization request for a predetermined time. After that, in step S515, the processor 240 inhibits power feeding control for the heater 127. Note that step S514 may be omitted.

Next, in step S516, using the display unit DISP of the user interface 116, the processor 240 can make a notification to promote exchange of the capsule 106. If the display unit DISP includes an LED, this notification can be causing the LED to blink in blue (repeat on/off). Hence, the user can exchange the capsule 106. In an example, one atomizer 104 and a plurality of (for example, three) capsules 106 can be sold as one set. In this example, after one atomizer 104 and all capsules 106 in one set are consumed, the atomizer 104 and the last capsule 106 in the consumed set can be exchanged with an atomizer 104 and a capsule 106 of a new set.

In step S517, the processor 240 waits for completion of the exchange of the capsule 106 (or the capsule 106 and the atomizer 104). In step S518, the processor 240 cancels inhibition of the power feeding control for the heater 127 and returns to step S501.

Figure 6A:
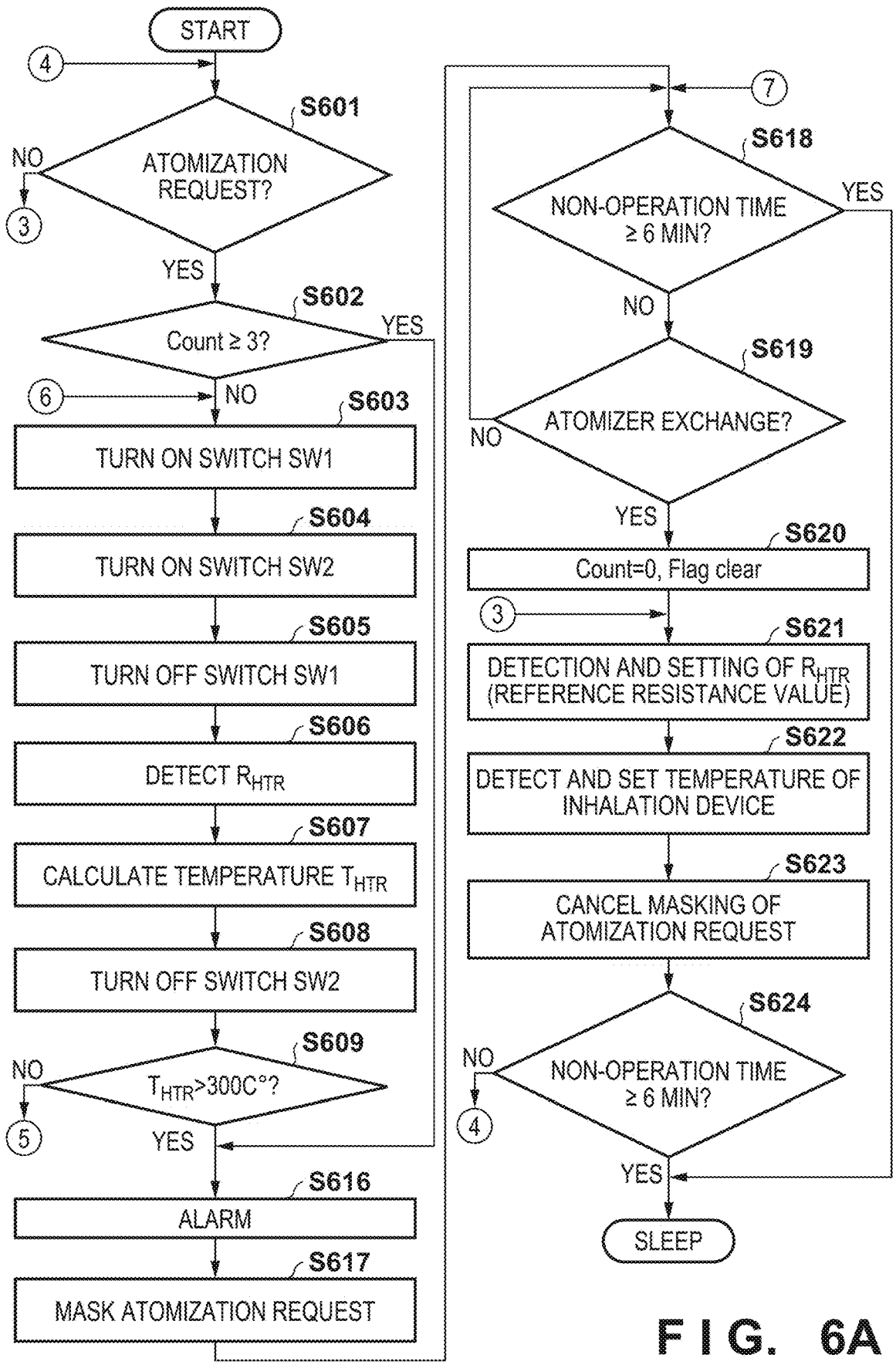
FIGS. 6A-6B are flowcharts showing detection associated processing of the inhalation device according to an embodiment.
Figure 6B:
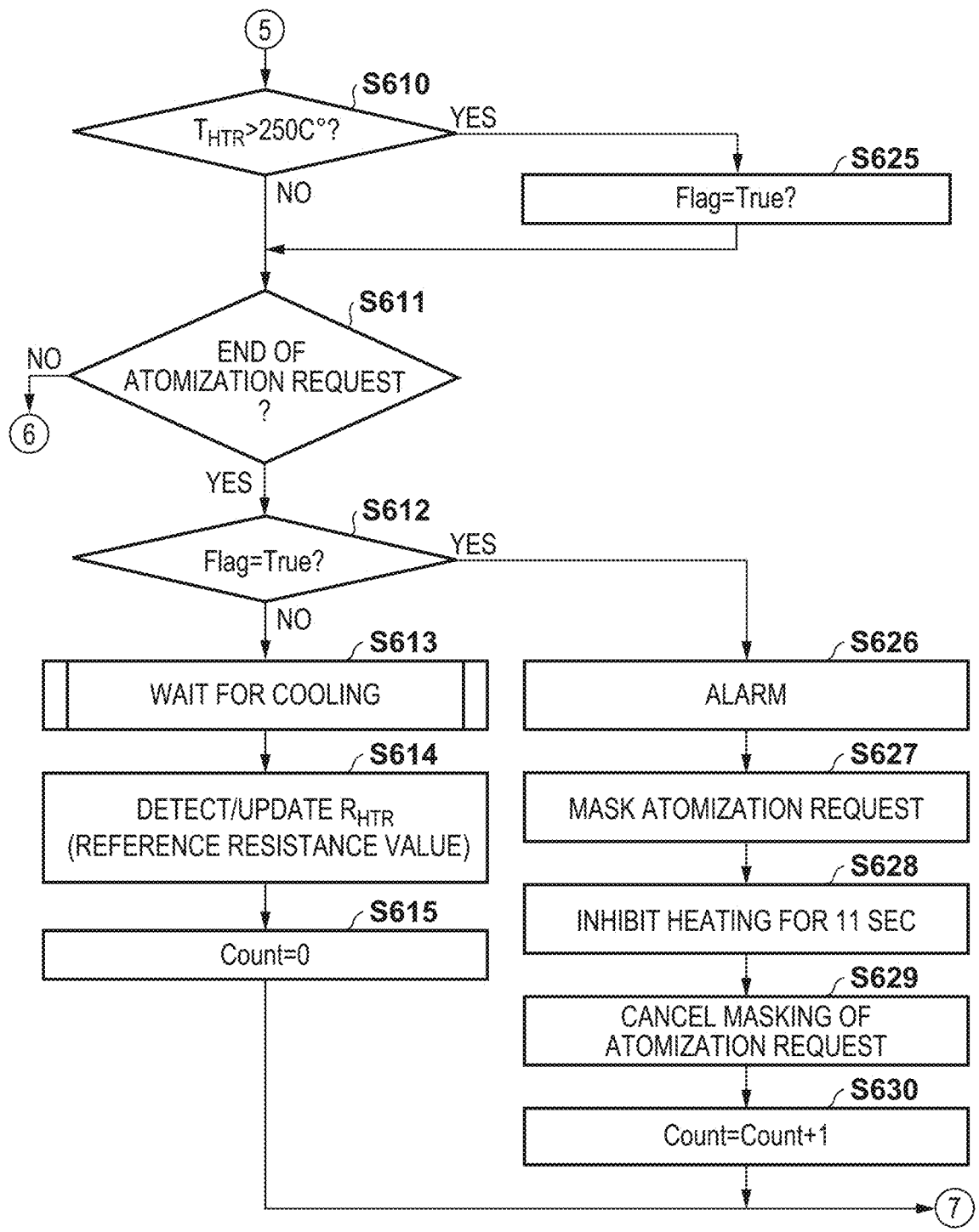

Detection associated processing concerning detection of the resistance value $R_{HTR}$ of the heater 127 and detection of the temperature of the heater 127 based on that will be described below. FIGS. 6A-6B show detection associated processing. Detection associated processing is executed by the processor 240 separately from the processing shown in FIGS. 5A-5B. The power feeding control described with reference to FIGS. 5A-5B can be executed based on the temperature of the heater 127 acquired by detection associated processing shown in FIGS. 6A-6B.

In step S601, the processor 240 determines whether an atomization request is received. If an atomization request is received, the process advances to step S602. If an atomization request is not received, the process advances to step S621. In step S602, the processor 240 determines whether Count that is a variable for control is equal to or larger than a predetermined number (for example, 3). If Count is equal to or larger than the predetermined number, the process advances to step S616. Otherwise, the process advances to step S603. Count is a variable that is incremented every time it is detected that the temperature of the heater 127 exceeds 250° C. That Count is equal to or larger than the predetermined number indicates that the aerosol source in the container 125 of the atomizer 104 is nearly exhausted or is completely exhausted. The value of the predetermined number can be determined in consideration of the detection error (including the influence of noise) of the temperature of the heater 127, and the like.

Steps S603 to S611 are processes performed during execution of heating processing (steps S503 to S507 in FIGS. 5A-5B). In step S603, the processor 240 turns on the switch SW1. In step S604, the processor 240 turns on the switch SW2. Next, in step S605, the processor 240 turns off the switch SW1. In this state, the resistance value $R_{HTR}$ of the heater 127 can be detected. In step S606, the processor 240 calculates the resistance value $R_{HTR}$ of the heater 127 in accordance with equations (2) and (4) based on the output voltage $V_{AMP}$ of the amplifier AMP of the detection circuit 220.

In step S607, the processor 240 calculates the resistance value $R_{HTR}$ of the heater 127 in accordance with equation (5) based on the resistance value $R_{HTR}$ of the heater 127 calculated in step S606 and reference temperature $T_{ref}$ and the reference resistance value $R_{ref}$ that are already set. Steps S606 and S607 correspond to processing of acquiring the temperature of the heater 127 based on the reference resistance value $R_{ref}$ and the information obtained using the detection circuit 220. In step S608, the processor 240 turns off the switch SW2.

In step S609, the processor 240 determines whether a temperature $T_{HTR}$ of the heater 127 exceeds 300° C. If the temperature $T_{HTR}$ exceeds 300° C. (the second temperature or the second threshold), the process advances to step S616. If the temperature $T_{HTR}$ is equal to or lower than 300° C., the process advances to step S610. In step S610, the processor 240 determines whether the temperature $T_{HTR}$ of the heater 127 exceeds 250° C. (the first temperature or the first threshold). If the temperature $T_{HTR}$ exceeds 250° C., the process advances to step S625. If the temperature $T_{HTR}$ is equal to or lower than 250° C., the process advances to step S611. In step S625, the processor 240 sets a flag Flag (that is, Flag=true). In this example, that the temperature $T_{HTR}$ of the heater 127 exceeds 250° C. (first temperature) indicates that the aerosol source in the container 125 of the atomizer 104 is nearly exhausted. That the temperature $T_{HTR}$ of the heater 127 exceeds 300° C. (second temperature) indicates that the aerosol source is completely exhausted. However, the first temperature and the second temperature can arbitrarily be determined in accordance with the type of the aerosol source, the structure of the transport portion (wick) 126, and the like.

In step S611, the processor 240 determines whether the atomization request has ended. If the atomization request has ended, the process advances to step S612. If the atomization request has not ended, the process returns to step S603. In step S612, the processor 240 determines whether the flag Flag is set. If the flag Flag is set, the process advances to step S626. If the flag Flag is not set, the process advances to step S613. That the flag Flag is set indicates that the temperature $T_{HTR}$ of the heater 127 exceeds 250° C.

In step S613, the processor 240 performs cooling determination processing of determining whether natural cooling of the heater 127 is completed. If a predetermined time has elapsed from the end of heating processing (that is, from the end of step S611), the processor 240 may determine that natural cooling of the heater 127 is completed. Alternatively, the processor 240 may detect the resistance value $R_{HTR}$ of the heater 127 and determine, based on the resistance value $R_{HTR}$, that natural cooling of the heater 127 is completed. A detailed example of step S613 will be described later.

Next to step S613, in step S614, the processor 240 detects the resistance value $R_{HTR}$ of the heater 127 using the detection circuit 220, and updates the reference resistance value $R_{ref}$ by the resistance value $R_{HTR}$. More specifically, the processor 240 turns on the switch SW2, detects the output voltage $V_{AMP}$ of the amplifier AMP, and after that, turns off the switch SW2. The processor 240 calculates the resistance value $R_{HTR}$ of the heater 127 in accordance with equations (2) and (4) based on the detected output voltage $V_{AMP}$, and stores the calculated resistance value $R_{HTR}$ as the reference resistance value $R_{ref}$ in the memory in association with (in linkage with) the reference temperature $T_{ref}$. In step S615, the processor 240 resets Count to 0.

The reference resistance value $R_{ref}$ at the reference temperature $T_{ref}$ can vary in, for example, each inhalation operation (puff operation) of the user because of the contact resistance between the electrical contact (111, 112) of the holding portion 103 of the controller 102 and the electrical contact (123, 124) of the heater 127, oxidation of the heater 127, and the like. For this reason, in step S614, the resistance value $R_{HTR}$ of the heater 127 is detected after the end of heating processing and before reception of the next atomization request, and the reference resistance value $R_{ref}$ is updated by the resistance value $R_{HTR}$, thereby accurately acquiring the temperature of the heater 127 during heating processing. In addition, step S614 is performed after it is determined in step S613 that natural cooling of the heater 127 is completed, that is, in a state in which the heater 127 is sufficiently naturally cooled, and the temperature of the heater 127 is stable. That is, since the resistance value $R_{HTR}$ is detected in a state in which the time fluctuation of the resistance value $R_{HTR}$ of the heater 127 is small and stable, the reliable reference resistance value $R_{ref}$ can be acquired.

Here, as the reference temperature $T_{ref}$ stored in the memory in association with the reference resistance value $R_{ref}$, for example, a constant (temperature) already stored in the memory as the reference temperature $T_{ref}$ may be used. In this case, the constant can arbitrarily be set by pre-verification or the like and is preferably set to a temperature higher than 27° C. that is generally called room temperature (R.T.). This is because a long time is needed to lower the temperature $T_{HTR}$ of the heater 127 to the room temperature (27° C.) by natural cooling. For example, the constant is set to an arbitrary temperature within the range of 30° C. to 50° C. or preferably to an arbitrary temperature within the range of 35° C. to 45° C., and is 40° C. as an example.

Alternatively, as the reference temperature $T_{ref}$ stored in the memory in association with the reference resistance value $R_{ref}$, for example, a temperature calculated based on the output value of the temperature sensor 282 may be used.

In this case, since the temperature sensor 282 detects the temperature of a component different from the heater 127, a correction value used to calculate (convert) the temperature of the heater 127 after cooling from the output value of the temperature sensor 282 (the temperature of the component) is preferably obtained by pre-verification. The correction value may have a form of a coefficient to be multiplied by the output value of the temperature sensor 282, or may have a form of a constant to be added to the output value. Note that the temperature sensor 282 may be a temperature sensor configured to detect the temperature of the power supply (battery) 250, as described above, or may be a temperature sensor provided in the puff sensor 281 to output a temperature-compensated pressure value. The temperature sensor of the puff sensor 281 can detect an outside air temperature.

If the processor 240 determines in step S609 that the temperature $T_{HTR}$ of the heater 127 exceeds 300° C., in step S616, the processor 240 makes a notification representing the occurrence of an abnormality (exhaustion of the aerosol source) using the display unit DISP of the user interface 116. If the display unit DISP includes an LED, this notification can be causing the LED to blink in red (repeat on/off).

Next, in step S617, the atomization request is masked (disabled). In a state in which the atomization request is masked, even if an atomization request is generated, it is neglected. That is, in a state in which the atomization request is masked, even if an atomization request is generated, it is determined in step S601 (also in step S501 of FIGS. 5A-5B) that the atomization request does not exist. Next, in step S618, the processor 240 determines whether the time (non-operation time) in which an operation by the user on the operation unit OP of the user interface 116 is not performed has reached a predetermined time (for example, 6 min). If the non-operation time has reached the predetermined time, the processor 240 transitions to a sleep state (sleep mode). Return from the sleep state can be done in response to, for example, an operation by the user on the operation unit OP of the user interface 116.

Until the non-operation time reaches the predetermined time, step S619 is executed. In step S619, the processor 240 waits for completion of the exchange work of the atomizer 104. More specifically, in step S619, the processor 240 waits for an operation of detaching the atomizer 104 from (the holding portion 103 of) the controller 102 and attaching a new atomizer 104 to (the holding portion 103 of) the controller 102. The processor 240 can determine completion of the exchange work of the atomizer 104 based on a change in the output voltage $V_{AMP}$ of the amplifier AMP of the detection circuit 220.

Here, when the atomizer 104 is detached from the holding portion 103, the heater 127 connected between the first electrical contact 111 and the second electrical contact 112 is lost. Hence, the output voltage $V_{AMP}$ of the amplifier AMP changes. Based on this, the processor 240 can detect the detachment of the atomizer 104 from the holding portion 103. When the atomizer 104 is attached to the holding portion 103, the heater 127 is connected between the first electrical contact 111 and the second electrical contact 112. Hence, the output voltage $V_{AMP}$ of the amplifier AMP changes. Based on this, the processor 240 can detect that the atomizer 104 is attached to the holding portion 103.

Upon detecting the exchange of the atomizer 104, in step S620, the processor 240 resets Count to 0 and clears Flag. Next, in step S621, the processor 240 detects the output voltage $V_{AMP}$ of the amplifier AMP, calculates the resistance value $R_{HTR}$ of the heater 127 in accordance with equations (2) and 4 based on the output voltage $V_{AMP}$, and stores the resistance value $R_{HTR}$ in the memory as the reference resistance value $R_{ref}$. Step S621 is processing of acquiring the reference resistance value $R_{ref}$ of the heater 127 of the atomizer 104 newly attached to (the holding portion 103 of) the controller 102. In the new atomizer 104, the characteristic (for example, the relationship between the reference temperature and the reference resistance value) of the heater 127 may be different from that in the atomizer 104 used so far because of a manufacturing error or individual difference. Hence, when step S621 is performed, the resistance value $R_{HTR}$ of the heater 127 of the atomizer 104 newly attached to the controller 102 can be detected as the reference resistance value $R_{ref}$ in a state in which power feeding is not performed yet (heating is not performed).

In step S622, the processor 240 acquires the temperature of a predetermined portion of the inhalation device 100 from the temperature sensor 282, and stores the temperature in the memory as the reference temperature $T_{ref}$. Here, a temperature difference may exist between the heater 127 and the predetermined portion of the inhalation device 100. Such a temperature difference may be neglected, or the temperature difference may be eliminated by the above-described correction value. Next, in step S623, masking of the atomization request is canceled.

In step S624, the processor 240 determines whether the non-operation time in which an operation by the user on the operation unit OP of the user interface 116 is not performed has reached a predetermined time (for example, 6 min). If the non-operation time has reached the predetermined time, the processor 240 transitions to the sleep state (sleep mode). On the other hand, if the non-operation time has not reached the predetermined time, the process returns to step S601.

If the flag Flag is set in step S612 described above, the process advances to step S626. In step S626, the processor 240 makes a notification representing the occurrence of an abnormality (temporary shortage of the aerosol source in the transport portion (wick) 126) using the display unit DISP of the user interface 116. If the display unit DISP includes an LED, this notification can be causing the LED to blink in red (repeat on/off). Next, in step S627, the processor 240 masks (disables) the atomization request. In step S628, the processor 240 inhibits heating of the heater 127 (power feeding to the heater 127) for a predetermined period (for example, 11 sec). Next, the processor 240 cancels masking of the atomization request in step S629, increments Count in step S630, and returns to step S618.

Figure 7:
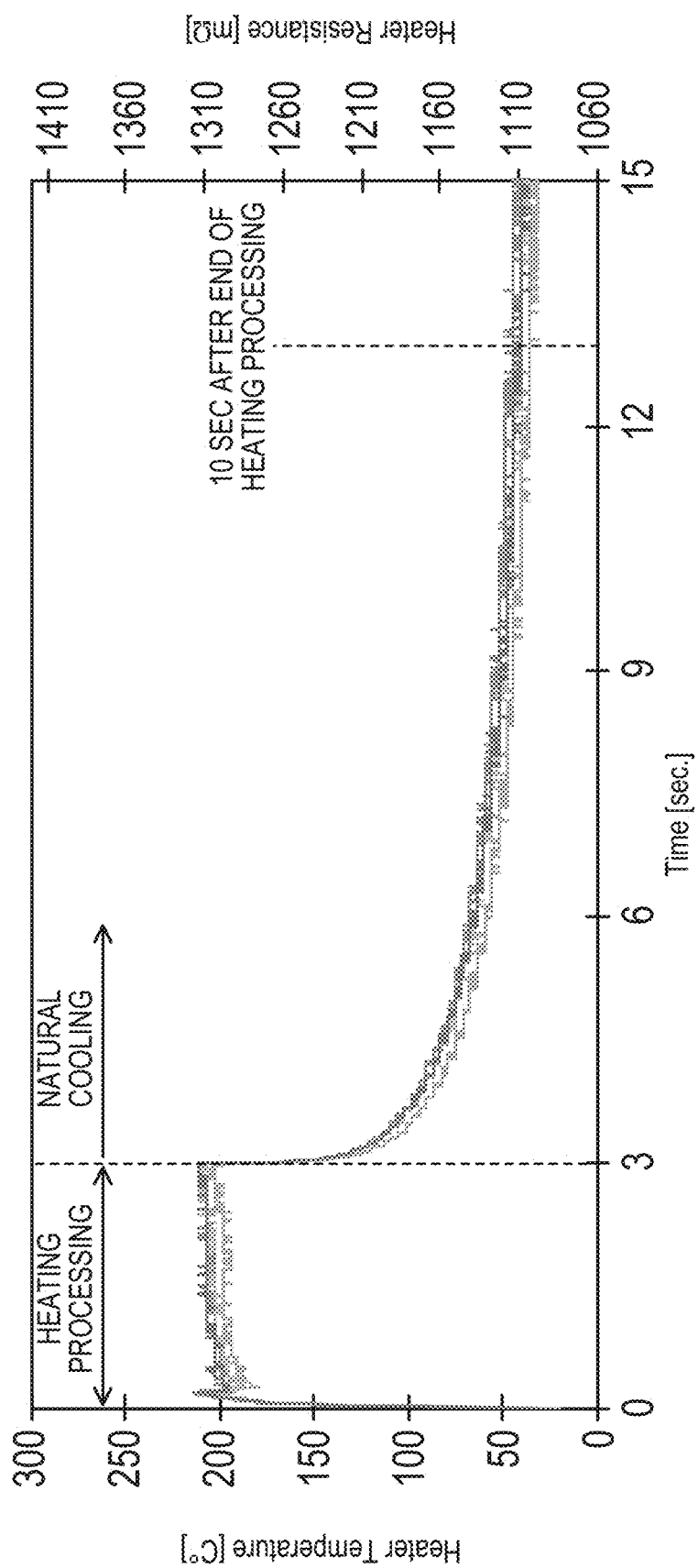
FIG. 7 is a view showing a verification example of the temporal changes of the temperature and the resistance value of a heater.
Figure 8:
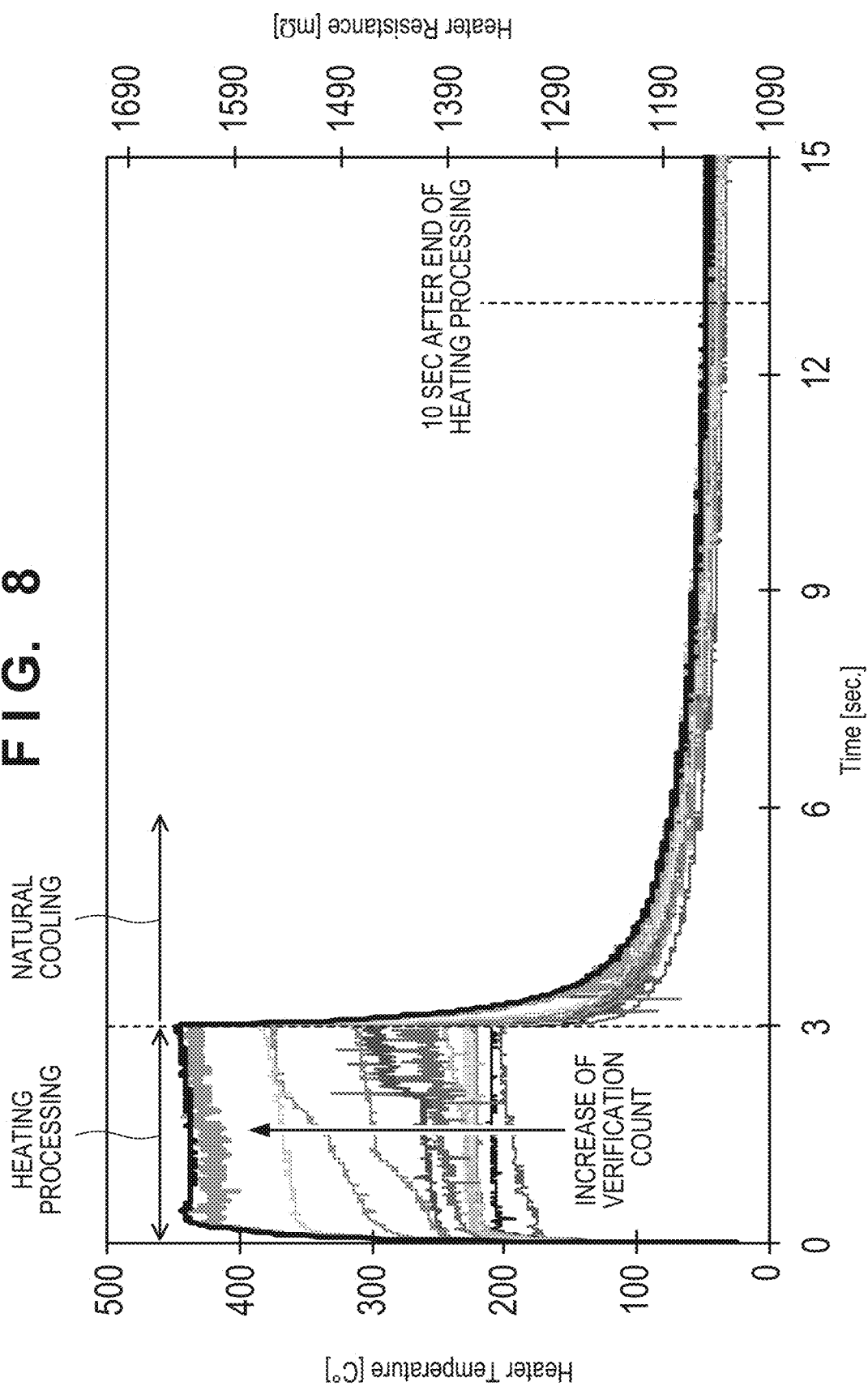
FIG. 8 is a view showing a verification example of the temporal changes of the temperature and the resistance value of the heater.

Details of cooling determination processing of step S613 in FIGS. 6A-6B will be described with reference to FIGS. 7 to 12. FIGS. 7 and 8 show verification examples of the temporal changes (time-rate changes) of the temperature and the resistance value of the heater 127 during and after execution of heating processing of the heater 127 (feeding to the heater 127). In FIGS. 7 and 8, the period of 0 to 3 sec is the period in which the heating processing of the heater 127 is being executed, and the period after the period of 3 sec is the period in which the heating processing of the heater 127 is ended, and natural cooling is performed. In FIGS. 7 and 8, the resistance value of the heater 127 (the ordinate on the right side) is a value calculated in accordance with equations (2) and (4) based on the output voltage $V_{AMP}$ of the amplifier AMP, and the temperature of the heater 127 (the ordinate on the left side) is a value calculated in accordance with equation (5) based on the calculated resistance value.

Figure 9:
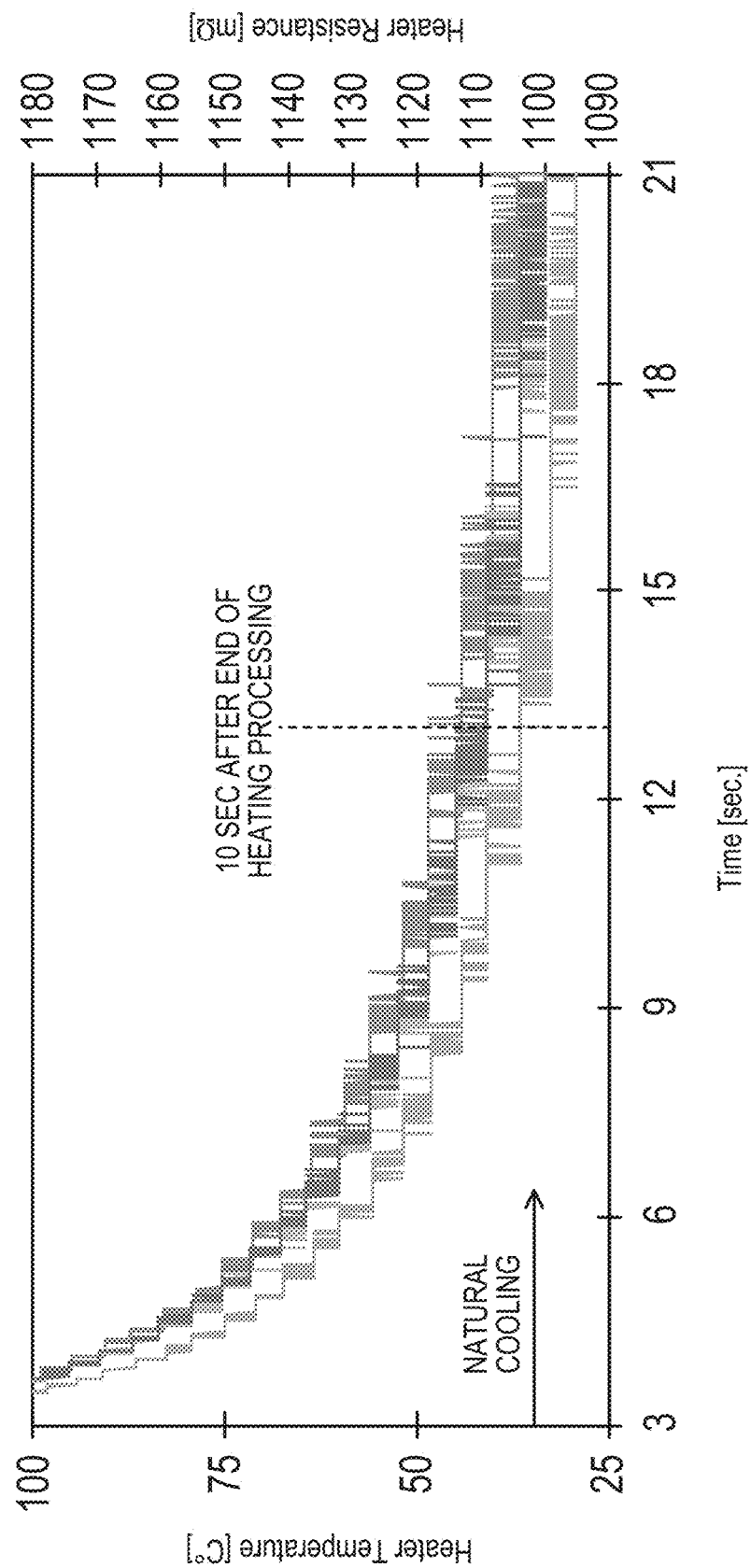
FIG. 9 is a view showing a verification example of the temporal changes of the temperature and the resistance value of the heater during natural cooling.

FIG. 7 shows an example in which verification of the temporal changes of the temperature and the resistance value of the heater 127 was performed a plurality of times (four times) in a state in which the aerosol source sufficiently existed in the container 125 of the atomizer 104, and the aerosol source was sufficiently supplied to the transport portion (wick) 126. In the example shown in FIG. 7, it is found that the temperature of the heater 127 during execution of heating processing (the period of 0 to 3 sec) is about 200° C. in the four verifications. FIG. 9 is an enlarged view showing the temporal changes of the temperature and the resistance value of the heater 127 under natural cooling after the end of heating processing (during the period after the period of 3 sec). It can be seen that the temporal changes of the temperature and the resistance value of the heater 127 stabilize about 10 sec after the end of heating processing (that is, about 13 sec after the start of heating processing). Here, the stabilization of the temporal change of the resistance value of the heater 127 can arbitrarily be defined, and may be defined as a state in which, for example, the temporal change ratio (gradient) of the resistance value of the heater 127 falls within an allowable range (for example, 10 mΩ/sec or less). As an example, it may be defined as a state in which the difference between the maximum resistance value and the minimum resistance value of the heater 127 during a predetermined time (for example, 3 sec) falls within an allowable range (for example, 10 mΩ/sec or less).

Figure 10:
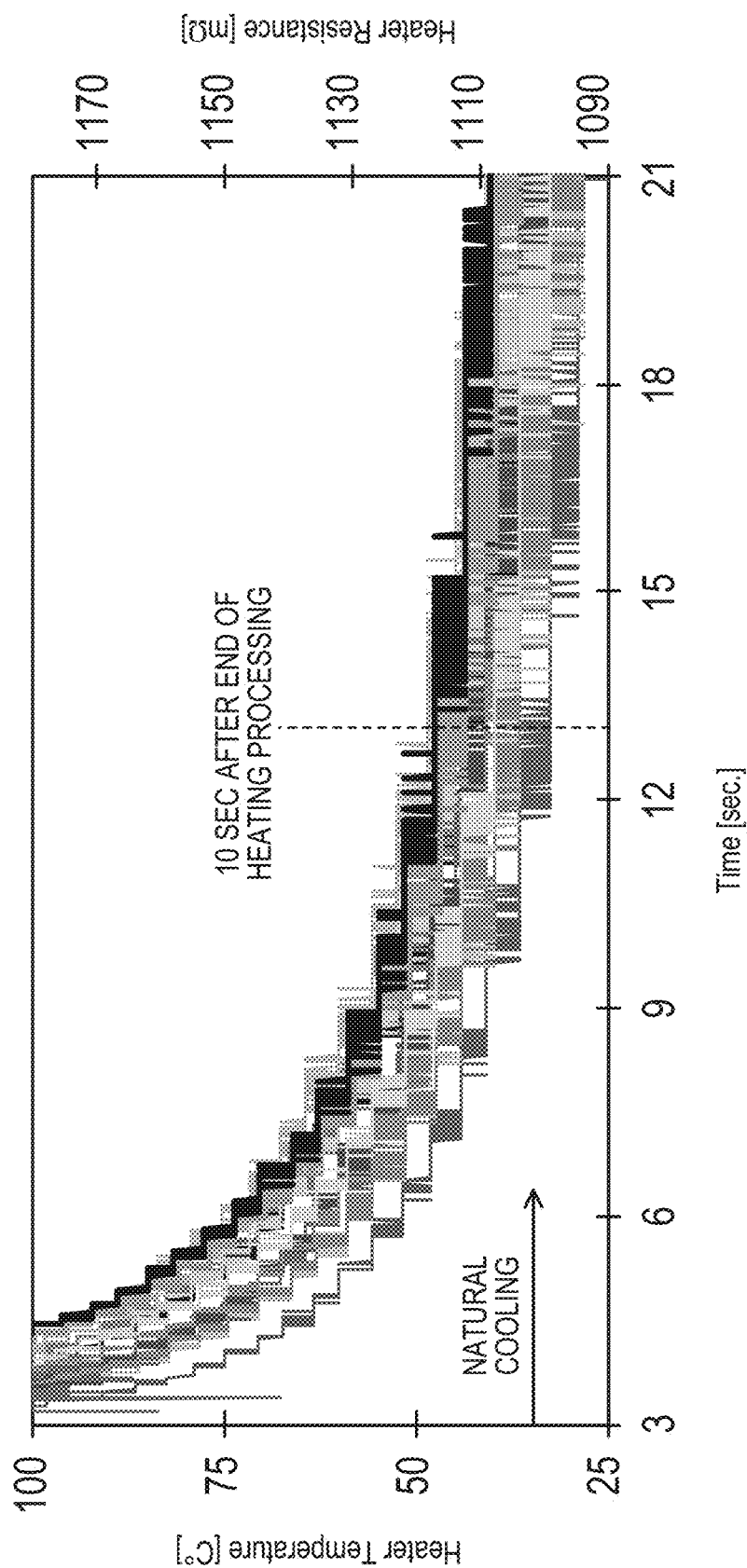
FIG. 10 is a view showing a verification example of the temporal changes of the temperature and the resistance value of the heater during natural cooling.

FIG. 8 shows an example in which verification of the temporal changes of the temperature and the resistance value of the heater 127 was performed a plurality of times in a state in which the aerosol source in the container 125 of the atomizer 104 was nearly exhausted, and the transport portion (wick) 126 started drying. In the example shown in FIG. 8, it is found that since the transport portion 126 dries along with an increase in the verification count, the temperature of the heater 127 increases during execution of heating processing (the period of 0 to 3 sec). FIG. 10 is an enlarged view showing the temporal changes of the temperature and the resistance value of the heater 127 under natural cooling after the end of heating processing (during the period after the period of 3 sec). It can be seen that the temporal changes of the temperature and the resistance value of the heater 127 stabilize about 10 sec after the end of heating processing (that is, about 13 sec after the start of heating processing). It is found that the resistance value converges to almost the same resistance value irrespective of the verification count.

According to the above-described verifications, it can be seen that when a predetermined time (for example, 10 sec) elapses from the end of heating processing, the resistance value converges to almost the same resistance value, and the temporal change of the resistance value of the heater 127 stabilizes regardless of the amount of the aerosol source in the container 125. That is, cooling determination processing (step S613) is preferably executed such that detection of the resistance value $R_{HTR}$ of the heater 127 as the reference resistance value $R_{ref}$ (step S614) is executed after the elapse of a predetermined time from the end of heating processing.

Figure 11:
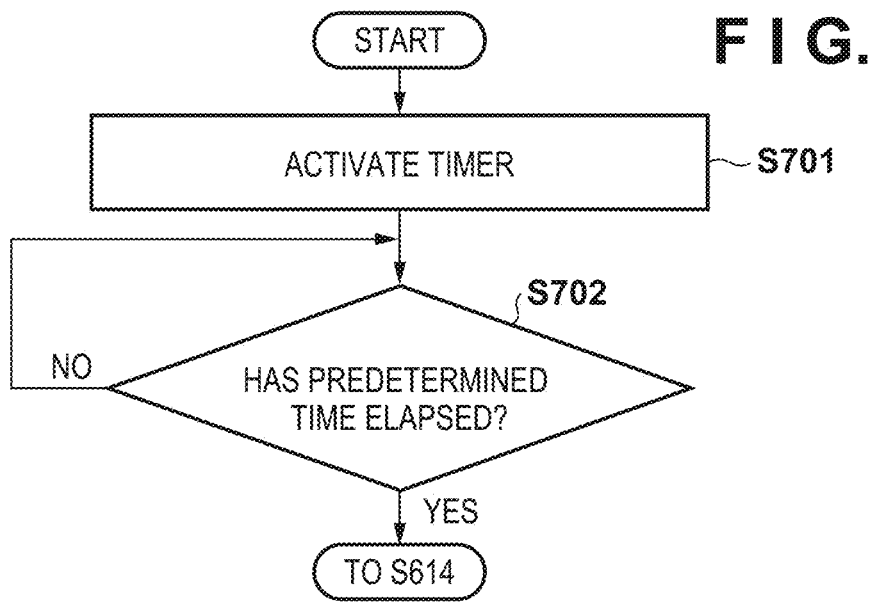
FIG. 11 is a flowchart showing the first example for providing details of cooling determination processing.

FIG. 11 shows the first example for providing details of cooling determination processing of step S613 in FIGS. 6A-6B. In step S701, the processor 240 activates a timer. For example, upon determining in step S611 that the atomization request has ended (that is, at the end of heating processing), the processor 240 activates the timer. In step S702, the processor 240 determines whether a preset predetermined time has elapsed, and if the predetermined time has elapsed, advances to step S614 in FIGS. 6A-6B. The predetermined time can be set to a time (for example, 10 sec) in which the temporal change of the resistance value of the heater 127 stabilizes in natural cooling after the end of heating processing, as described above.

Figure 12:
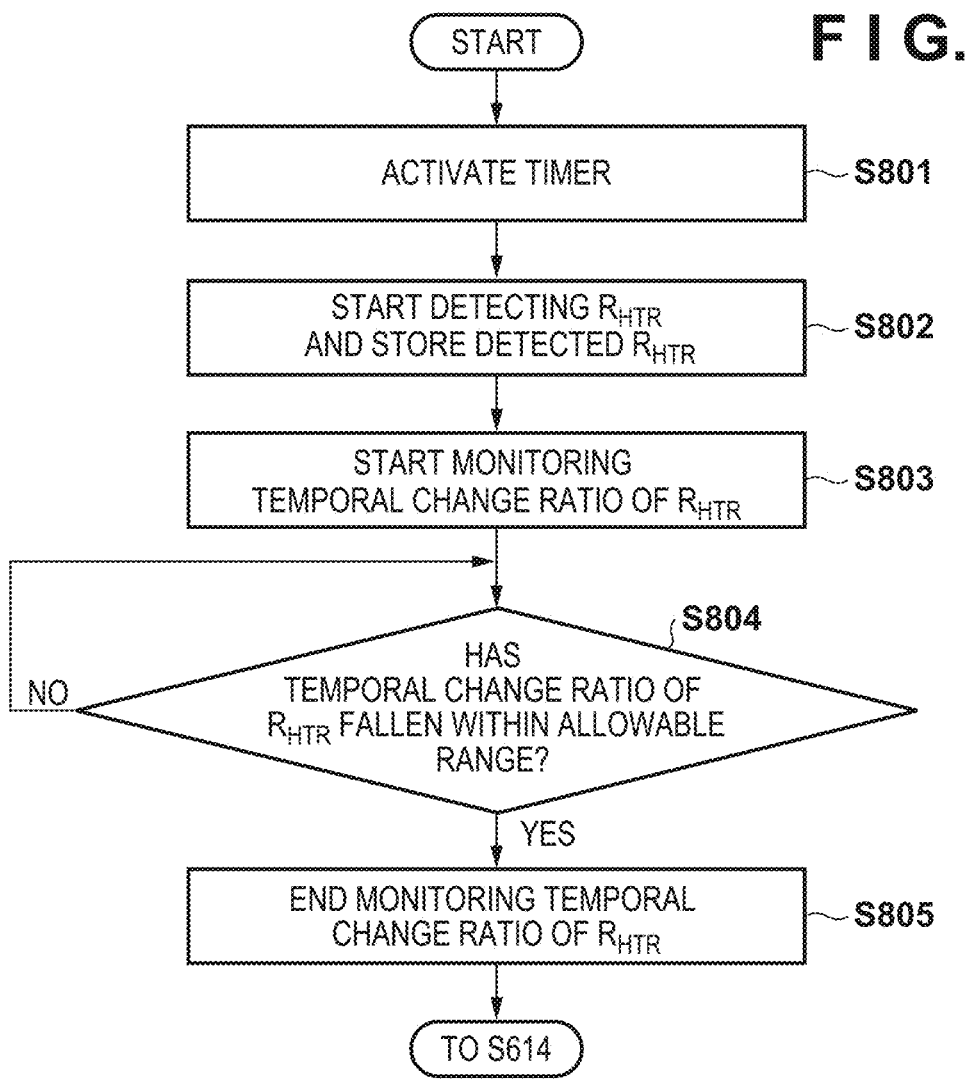
FIG. 12 is a flowchart showing the second example for providing details of cooling determination processing.

FIG. 12 shows the second example for providing details of cooling determination processing of step S613 in FIGS. 6S-6B. In step S801, the processor 240 activates a timer. For example, upon determining in step S611 that the atomization request has ended (that is, at the end of heating processing), the processor 240 activates the timer. Next, in step S802, the processor 240 starts detecting the resistance value $R_{HTR}$ of the heater 127. In step S803, the processor 240 starts monitoring the temporal change ratio (time-rate change ratio) of the resistance value $R_{HTR}$ of the heater 127. For example, the processor 240 turns on the switch SW2, detects the output voltage $V_{AMP}$ of the amplifier AMP, and calculates the resistance value $R_{HTR}$ of the heater 127 in accordance with equations (2) and (4) based on the output voltage $V_{AMP}$. The processor 240 performs detection (calculation) of the resistance value $R_{HTR}$ of the heater 127 periodically (for example, at a period of 10 msec), and stores the detected resistance value $R_{HTR}$ of the heater 127 in the memory in linkage with the elapsed time from the end of heating processing.

Next, in step S804, the processor 240 determines whether the temporal change ratio of the resistance value $R_{HTR}$ of the heater 127 falls within an allowable range. As an example, the processor 240 determines whether the difference between a maximum resistance value $MAX(R_{HTR})$ and a minimum resistance value $MIN(R_{HTR})$ of the heater 127 during the time between the current time and a time retroactive from the current time by a predetermined time (for example, 3 sec) falls within an allowable range (for example, 10 mΩ or less). Step S803 is executed until the difference falls within the allowable range. On the other hand, if the difference falls within the allowable range, in step S805, the processor 240 ends monitoring the temporal change ratio of the resistance value $R_{HTR}$ of the heater 127 and then advances to step S614 in FIGS. 6A-6B.

Here, in the second example shown in FIG. 12, the above-described first example shown in FIG. 11 may be applied. More specifically, step S702 of the first example shown in FIG. 11 may be applied between step S801 and step S802 of the second example shown in FIG. 12. In this case, step S802 is executed after the elapse of a predetermined time (for example, 10 sec) from the end of heating processing. Since this decreases the number of times of energizing the heater 127 to acquire the resistance value $R_{HTR}$ of the heater 127, the time until affirmative determination is done in step S804 can be shortened.

<Another Example of Detection Associated Processing>

Figure 13A:
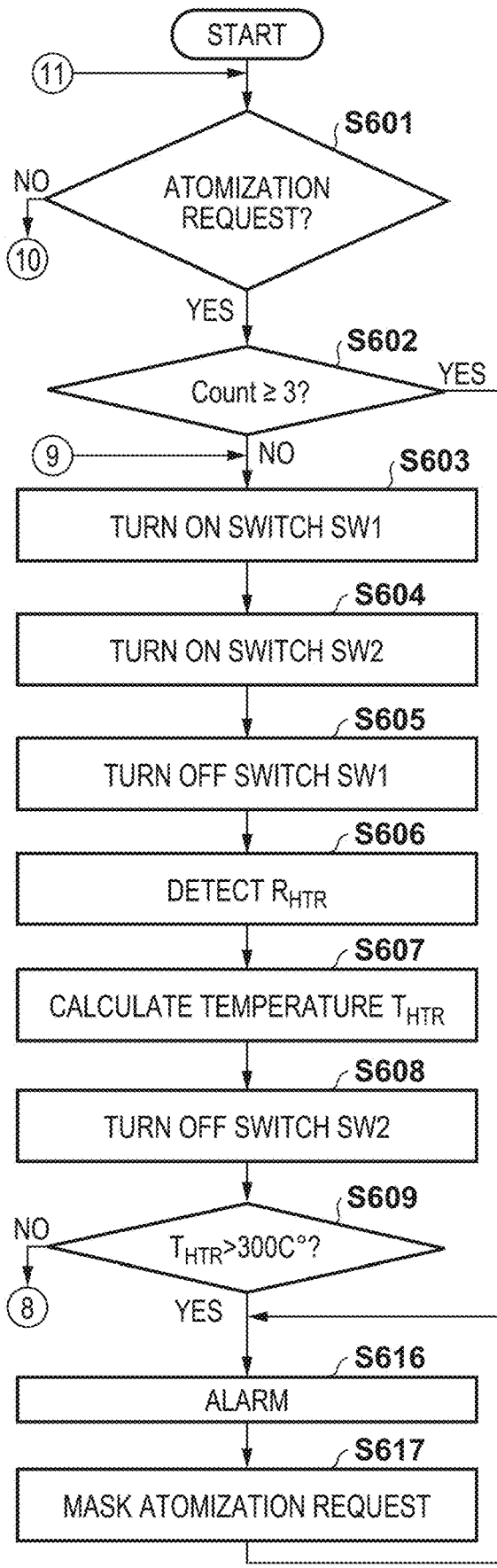
FIGS. 13A-13B are flowcharts showing another example of detection associated processing of the inhalation device.
Figure 13B:
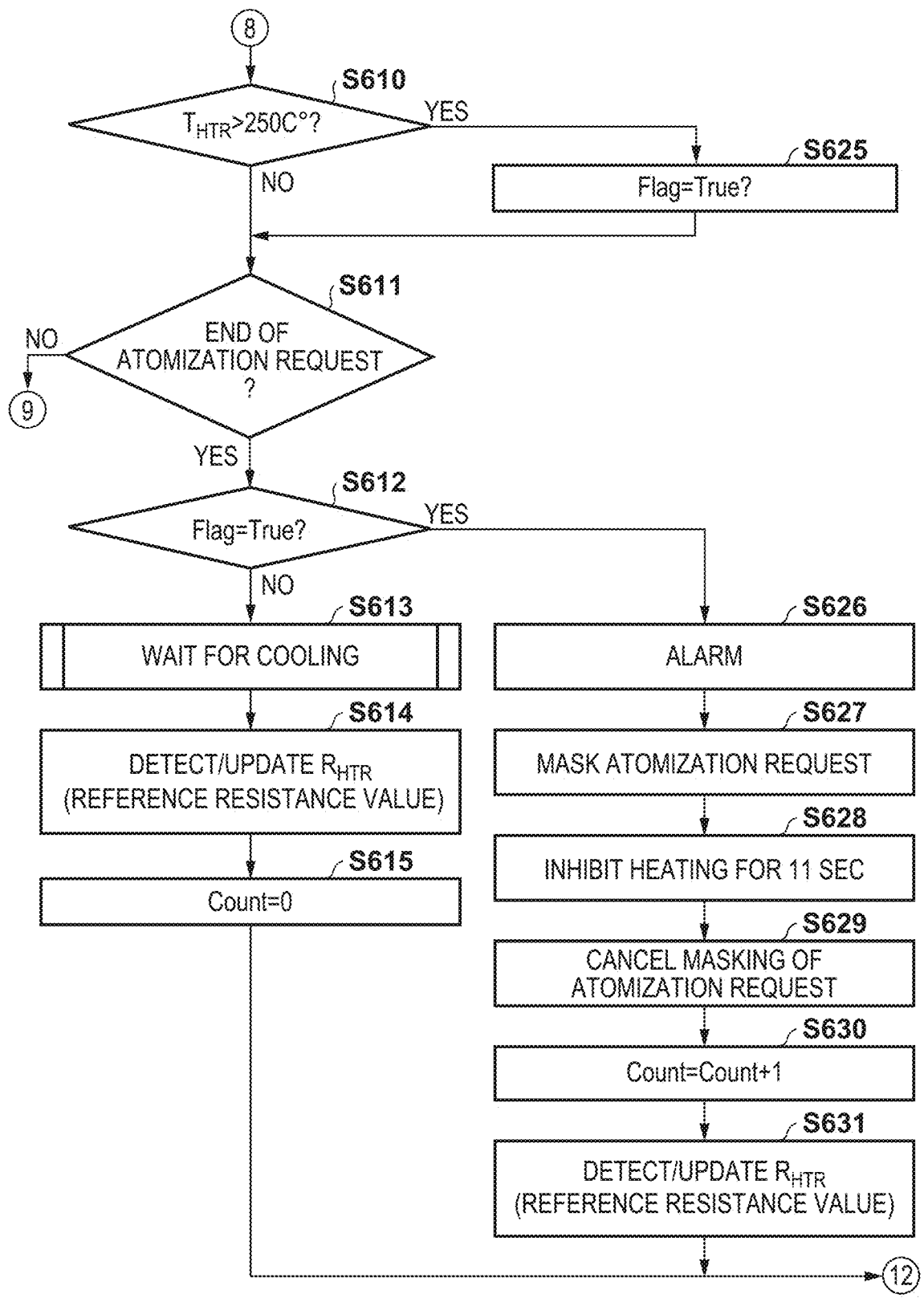

Another example of detection associated processing concerning detection of the resistance value $R_{HTR}$ of the heater 127 and detection of the temperature of the heater 127 based on that will be described next. FIGS. 13A-13B show another example of detection associated processing. The flowcharts of FIGS. 13A-13B are basically the same as the flowcharts of FIGS. 6A-6B except that steps S631 and S632 are further added. Note that in the example shown in FIGS. 13A-13B, both steps S631 and S632 are executed. However, the present invention is not limited to this, and one of steps S631 and S632 may be executed.

Step S631 is arranged between step S630 and step S618. In step S631, the processor 240 detects the resistance value $R_{HTR}$ of the heater 127 using the detection circuit 220, and updates the reference resistance value $R_{ref}$ by the resistance value $R_{HTR}$, as in step S614. Since step S631 is performed after step S628 of inhibiting heating of the heater 127 for a predetermined period (for example, 11 sec), the heater 127 is sufficiently cooled, and the temperature of the heater 127 is stabilized. Hence, when the reference resistance value $R_{ref}$ is updated by the resistance value $R_{HTR}$ of the heater 127 detected in this state, the reliable reference resistance value $R_{ref}$ can be acquired. Note that step S631 need not always be arranged between step S630 and step S618, and can be executed at an arbitrary timing after step S628 and before the next atomization request. Step S631 may be executed during step S628 (that is, during a predetermined time in which heating of the heater 127 is inhibited). In this case, step S631 is preferably executed after stabilization of the temperature of the heater 127 (for example, after waiting for the time (about 10 sec) set in advance to stabilize the temperature of the heater 127), and is particularly preferably executed immediately before the elapse of a predetermined time in step S628. After the time of about 10 sec elapses from the end of heating processing, the temporal changes of the temperature and the resistance value of the heater 127 stabilize, as described above. Hence, even before the elapse of the predetermined time in step S628, the reliable reference resistance value $R_{ref}$ can be acquired.

Step S632 is executed before the transition to the sleep state (sleep mode) if it is determined in step S618 or S624 that the non-operation time has reached a predetermined time (for example, 6 min). In step S632 as well, the processor 240 detects the resistance value $R_{HTR}$ of the heater 127 using the detection circuit 220, and updates the reference resistance value $R_{ref}$ by the resistance value $R_{HTR}$, as in step S614 or S631. Since the heater 127 is sufficiently cooled, and the temperature of the heater 127 is stabilized even at the timing of transition to the sleep state, the reliable reference resistance value $R_{ref}$ can be acquired.

Figure 14:
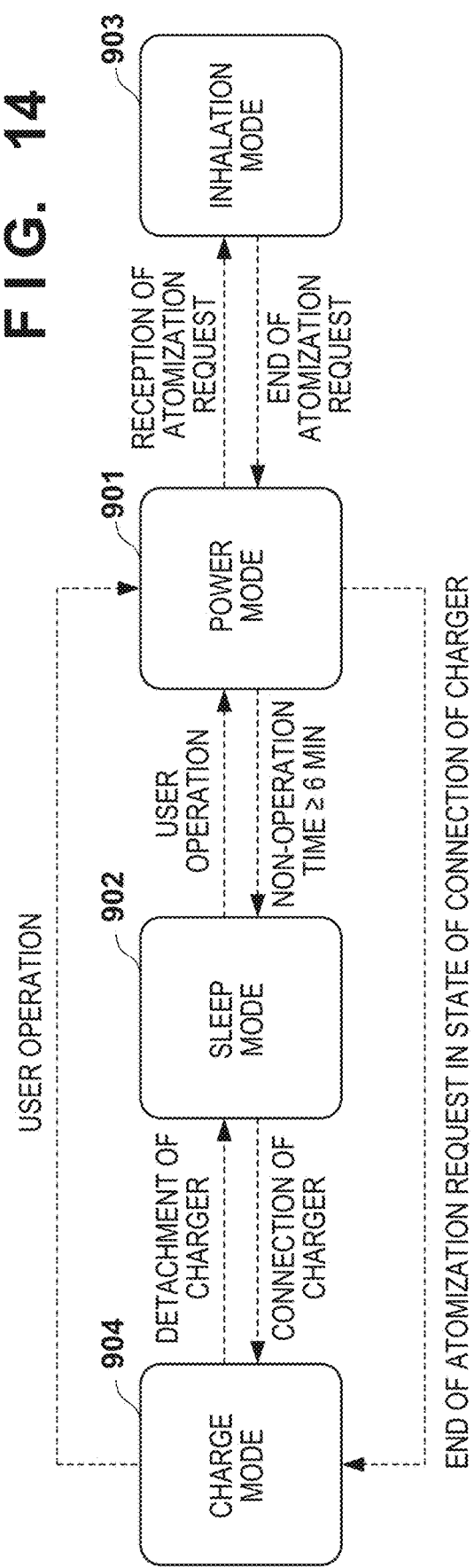
FIG. 14 is a view showing an example of operation modes of a processor.

Operation modes of the processor 240 will be described here. FIG. 14 shows an example of operation modes of the processor 240. The processor 240 can include, as operation modes, for example, a power mode 901, a sleep mode 902, an inhalation mode 903, and a charge mode 904. The above-described processes shown in FIGS. 5A-5B, 6A-6B, and 13A-13B can be executed in the states of the power mode 901 and the inhalation mode 903. The power mode 901 is a state in which power feeding to the puff sensor 281 is being performed, and is a mode (first mode) in which heating processing can be executed in accordance with reception of an atomization request. In the state of the power mode 901, the puff sensor 281 detects that the user performs the inhalation operation via the mouthpiece portion 130. Upon receiving an atomization request from the puff sensor 281, the processor 240 transitions from the power mode 901 to the inhalation mode 903. The inhalation mode 903 is a mode in which heating processing is executed by supplying power to the heater 127. When the atomization request ends, the processor 240 transitions from the inhalation mode 903 to the power mode 901.

If the non-operation time has reached a predetermined time (for example, 6 min), the processor 240 transitions from the power mode 901 to the sleep mode 902. The sleep mode 902 is a mode (second mode) in which power feeding to the puff sensor 281 is stopped to make power consumption smaller than in the power mode 901. If an operation by the user on the operation unit OP (for example, long press on the operation unit OP (switch) by the user) is detected, the processor 240 transitions from the sleep mode 902 to the power mode 901.

The charge mode 904 is a mode in which the power supply (battery) 250 is charged. If a charger is connected to a charge port (for example, a USB port) provided in the controller 102, the processor 240 transitions from the sleep mode 902 to the charge mode 904. On the other hand, if the charger is detached from the charge port of the controller 102, the processor 240 transitions from the charge mode 904 to the sleep mode 902. In addition, if an operation of the user (for example, long press on the operation unit OP by the user) is detected in a state in which the charger is connected to the charge port of the controller 102 (the state of the charge mode 904), the processor 240 interrupts charge of the power supply 250 and transitions from the charge mode 904 to the power mode 901. If the atomization request has ended in this case, the processor 240 transitions from the power mode 901 to the charge mode 904 to resume charge of the power supply 250.

OTHER EMBODIMENTS

Figure 15:
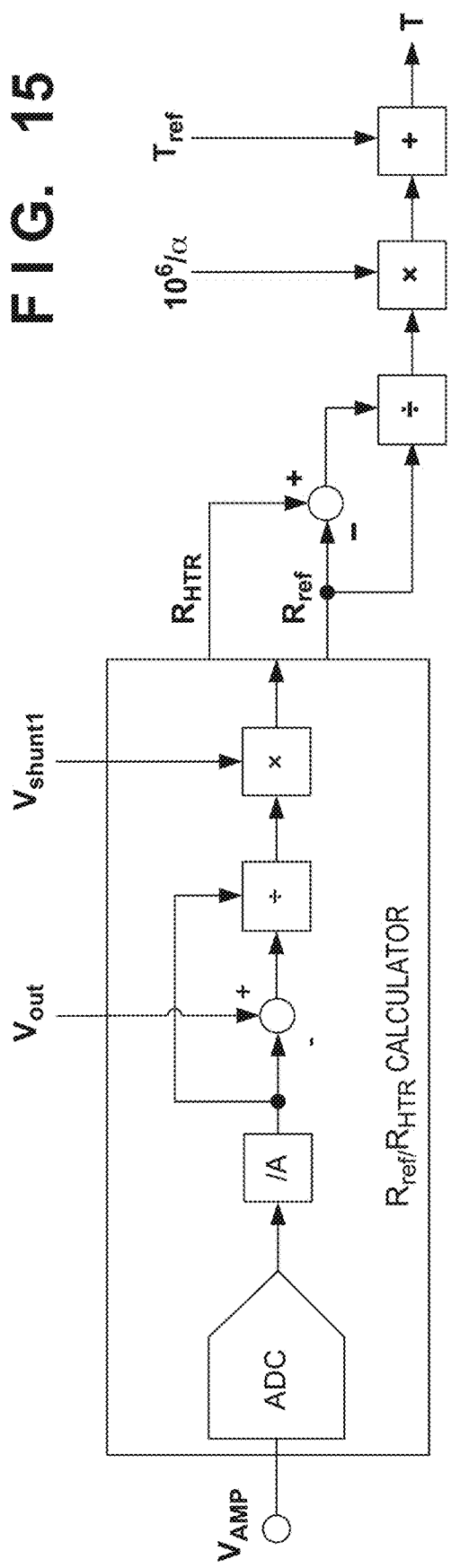
FIG. 15 is a view showing a detailed example in which calculation of a resistance value $R_{HTR}$ of a heater is implemented by an analog circuit.

Calculations exemplified by equations (2) and (4) may be implemented by an analog circuit. FIG. 15 shows an analog circuit that calculates the resistance value $R_{HTR}$ of the heater 127 in accordance with equations (2) and (4). Such an analog circuit may be incorporated in the MCU that constitutes the processor 240 or may be provided separately from the MCU. In detection associated processing shown in FIGS. 6 and 13, the temperature $T_{HTR}$ of the heater 127 is calculated in step S607 based on the resistance value $R_{HTR}$ of the heater 127 calculated in step S606. However, step S607 may be omitted. Note that in this case, each of the second temperature in step S609 and the first temperature in step S610 needs to be converted into a resistance value using equation (5). That is, in step S609, the processor 240 determines whether the resistance value $R_{HTR}$ of the heater 127 calculated in step S606 exceeds the resistance value converted from the second temperature (300° C.). Additionally, in step S610, the processor 240 determines whether the resistance value $R_{HTR}$ of the heater calculated in step S606 exceeds the resistance value converted from the first temperature (250° C.).

The invention is not limited to the foregoing embodiments, and various variations/changes are possible within the spirit of the invention.

What is claimed is:

1. A controller for an inhalation device, comprising:
a power supplier configured to supply power to a heater used to heat and atomize an aerosol source;
a detection circuit configured to detect a resistance value of the heater; and
a processor configured to execute heating processing of heating the aerosol source by controlling the power supplier to supply the power to the heater in accordance with reception of an atomization request of the aerosol source,
wherein the processor
controls the heating processing based on the resistance value of the heater detected using the detection circuit during the heating processing, a reference temperature of the heater, and a reference resistance value of the heater at the reference temperature,
performs cooling determination processing of determining whether natural cooling of the heater is completed after the end of the heating processing according to reception of the atomization request,
detects a resistance value of the heater using the detection circuit in a case of determining that the natural cooling is completed in the cooling determination processing, and
updates the reference resistance value by the resistance value of the heater detected using the detection circuit after an end of the heating processing and before the reception of the next atomization request,
wherein in the cooling determination processing, the processor
starts monitoring a temporal change ratio of the resistance value of the heater detected using the detection circuit after the end of the heating processing, and
determines that the natural cooling of the heater is completed, in a case where the temporal change ratio falls within an allowable range.

2. The controller according to claim 1, wherein the processor starts monitoring the temporal change ratio after an elapse of a predetermined time from the end of the heating processing.

3. The controller according to claim 1,
wherein the processor
inhibits the heating processing according to the reception of the atomization request during a predetermined period in a case where an obtained temperature of the heater exceeds a threshold, and
updates the reference resistance value by the resistance value of the heater detected using the detection circuit after stabilization of the temperature of the heater during the predetermined period or after an elapse of the predetermined period.

4. The controller according to claim 1,
wherein the processor
has, as operation modes, a first mode in which the heating processing can be executed in accordance with the reception of the atomization request and a second mode in which power consumption is smaller than in the first mode, and
updates the reference resistance value by the resistance value of the heater detected using the detection circuit when transitioning from the first mode to the second mode.

5. The controller according to claim 1, further comprising a memory configured to store the reference temperature,
wherein the processor obtains the temperature of the heater during the heating processing using the reference temperature stored in the memory.

6. The controller according to claim 5, wherein the reference temperature is set to a temperature within a range of 30° C. to 50° C.

7. The controller according to claim 1, further comprising a temperature sensor configured to detect a temperature of a component different from the heater,
wherein the processor sets the reference temperature based on an output value of the temperature sensor in response to a determination that the natural cooling of the heater is completed.

8. The controller according to claim 7, further comprising a pressure sensor configured to detect a puff operation of a user,
wherein the pressure sensor includes the temperature sensor to output a temperature-compensated pressure value.

9. The controller according to claim 7, further comprising a battery,
wherein the temperature sensor detects a temperature of the battery.

10. The controller according to claim 7, wherein the processor sets, as the reference temperature, a value obtained by converting the output value of the temperature sensor into the temperature of the heater.

11. The controller according to claim 1, wherein the processor performs the cooling determination processing and updates the reference resistance value, for each atomization request.

12. The controller according to claim 1, wherein the processor activates a timer when the heating processing according to reception of the atomization request is ended, and performs the cooling determination processing based on the timer.

* * * * *